United States Patent
Namoto et al.

(10) Patent No.: US 11,377,648 B2
(45) Date of Patent: Jul. 5, 2022

(54) POLYPEPTIDES HAVING ALPHA-AMYLASE ACTIVITY AND POLYNUCLEOTIDES ENCODING SAME

(71) Applicant: NOVOZYMES A/S, Bagsvaerd (DK)

(72) Inventors: Tomoko Namoto, Chiba (JP); Takashi Nakanishi, Chiba (JP); Shiro Fukuyama, Chiba (JP); Noriko Tsutsumi, Chiba (JP); Keiichi Ayabe, Konakadaicho (JP)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 17/045,903

(22) PCT Filed: Apr. 8, 2019

(86) PCT No.: PCT/EP2019/058771
§ 371 (c)(1),
(2) Date: Oct. 7, 2020

(87) PCT Pub. No.: WO2019/197318
PCT Pub. Date: Oct. 17, 2019

(65) Prior Publication Data
US 2021/0139875 A1    May 13, 2021

(30) Foreign Application Priority Data
Apr. 9, 2018  (EP) ................... 18166236

(51) Int. Cl.
| | |
|---|---|
| *C12N 9/30* | (2006.01) |
| *C12P 7/06* | (2006.01) |
| *C12P 19/02* | (2006.01) |
| *C12P 19/14* | (2006.01) |
| *C12N 15/52* | (2006.01) |
| *C12N 15/62* | (2006.01) |
| *C12N 15/82* | (2006.01) |
| *C12N 1/16* | (2006.01) |

(52) U.S. Cl.
CPC ............. *C12N 9/242* (2013.01); *C12N 1/16* (2013.01); *C12N 15/52* (2013.01); *C12N 15/62* (2013.01); *C12N 15/8245* (2013.01); *C12P 7/06* (2013.01); *C12P 19/02* (2013.01); *C12P 19/14* (2013.01); *C12Y 302/01001* (2013.01)

(58) Field of Classification Search
None
See application file for complete search history.

(56) References Cited

U.S. PATENT DOCUMENTS

2021/0139875 A1*  5/2021  Namoto ............... C12N 9/242

FOREIGN PATENT DOCUMENTS

| WO | 90/00609 A1 | 1/1990 |
| WO | 94/24158 A1 | 10/1994 |
| WO | 95/16782 A1 | 6/1995 |
| WO | 2004/055178 A1 | 7/2004 |
| WO | 2006/069290 A2 | 6/2006 |
| WO | 2013/006756 A2 | 1/2013 |

OTHER PUBLICATIONS

UniProt Accession No. A0A2J6PIP8_9HELO, published Mar. 28, 2018 (Year: 2018).*
Greenwood et al., 1994, Biotechnol Bioeng 44, 1295-1305.
Liu, 2018, EBI Accession No. KU886204.
Martino et al., 2018, EBI Accession No. A0A2J6PIP8.

\* cited by examiner

Primary Examiner — Richard C Ekstrom
(74) Attorney, Agent, or Firm — David A. Fazzolare

(57) ABSTRACT

The present invention relates to a hybrid polypeptide having alpha-amylase activity, selected from a first polypeptide sequence comprising a catalytic core, and a second polypeptide sequence comprising a carbohydrate binding module (CBM), wherein (a) the catalytic core is selected from a polypeptide having at least 80%, at least 85%, at least 90%, at least 91%, at least 92%, at least 93%, at least 94%, at least 95%, at least 96%, at least 97%, at least 98%, at least 99% or 100% sequence identity to amino acids 20 to 494 of SEQ ID NO: 1 or amino acids 20 to 496 of SEQ ID NO: 1; and (b) the CBM is selected from a polypeptide having at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 4, SEQ ID NO: 5, or SEQ ID NO: 6. The invention also relates to nucleic acid constructs, vectors, and host cells comprising the polynucleotides as well as methods of producing and using the polypeptides, and catalytic domains.

20 Claims, No Drawings
Specification includes a Sequence Listing.

SEQUENCE LISTING

```
<160> NUMBER OF SEQ ID NOS: 24

<210> SEQ ID NO 1
<211> LENGTH: 496
<212> TYPE: PRT
<213> ORGANISM: Acidomyces acidothermus

<400> SEQUENCE: 1

Met Arg Ser Phe Ser Ala Phe Leu Pro Leu Ala Ser Met Ile Thr Ala
1               5                   10                  15

Thr Phe Ala Leu Thr Pro Ala Gln Trp Arg Gly Gln Ser Ile Tyr Gln
            20                  25                  30

Val Leu Thr Asp Arg Phe Gly Arg Thr Asp Ser Thr Thr Ala Ala
        35                  40                  45

Cys Asp Val Asn Asp Tyr Cys Gly Gly Ser Trp Gln Gly Ile Ile Asn
    50                  55                  60

His Leu Asp Tyr Ile Gln Asp Met Gly Phe Ser Ala Ile Trp Ile Ser
65                  70                  75                  80

Pro Val Val Glu Asn Leu Val Gly Asp Thr Gln Asp Gly Ser Ala Tyr
                85                  90                  95

His Gly Tyr Trp Ala Gln Asn Ile Tyr Ala Leu Asn Pro Asn Phe Gly
            100                 105                 110

Thr Val Ser Asp Leu Val Ala Leu Ser Ala Ala Leu His Gln Arg Gly
            115                 120                 125

Met Tyr Leu Met Val Asp Val Val Thr Asn His Met Gly Tyr Asp Gly
130                 135                 140

Cys Gly Asp Cys Val Asp Tyr Ser Val Phe Thr Pro Phe Asn Ser Gln
145                 150                 155                 160

Ser Tyr Phe His Pro Phe Cys Leu Ile Asp Tyr Asn Asn Ser Thr Ser
                165                 170                 175

Ile Lys Val Cys Trp Glu Gly Asp Asn Ile Val Ser Leu Pro Asp Met
            180                 185                 190

Arg Thr Glu Asp Ser Asp Val Ala Thr Glu Trp Asn Thr Trp Ile Ser
            195                 200                 205

Glu Leu Val Ser Asn Tyr Ser Ile Asp Gly Leu Arg Ile Asp Ser Ala
    210                 215                 220

Gln Gln Val Asp Asn Ala Phe Phe Pro Phe Gln Ala Ala Ala Gly
225                 230                 235                 240

Gly Ile His Val Leu Gly Glu Val Phe Asn Gly Asp Pro Asn Tyr Val
                245                 250                 255

Cys Pro Tyr Gln Asp Phe Met Ser Gly Val Leu Asn Tyr Pro Ala Tyr
            260                 265                 270

Tyr Tyr Ile Thr Gln Ala Phe Gln Ser Thr Ser Gly Ser Ile Ser Asn
            275                 280                 285

Leu Val Asn Gly Ile Asn Gln Met Lys Ser Thr Cys Thr Asp Thr Thr
        290                 295                 300

Leu Leu Gly Ser Phe Leu Glu Asn His Asp Asn Pro Arg Phe Pro Ser
305                 310                 315                 320

Tyr Thr Ser Asp Leu Ser Leu Asp Lys Asn Ala Ile Thr Phe Thr Ile
```

```
                    325                 330                 335
Leu Gln Asp Gly Ile Pro Ile Ile Tyr Glu Gly Gln Glu His Tyr
            340                 345                 350

Ser Gly Gly Thr Val Pro Asn Asn Arg Glu Ala Ile Trp Leu Ser Gly
            355                 360                 365

Tyr Asp Lys Ser Ala Pro Leu Tyr Thr Trp Ile Ala Ser Val Asn Gln
            370                 375                 380

Ile Arg Asn Gln Ala Ile Phe Lys Asp Ser Asn Tyr Leu Thr Tyr Met
385                 390                 395                 400

Ala Trp Pro Ile Tyr Ser Asp Ala Ser Thr Ile Ala Met Arg Lys Gly
                405                 410                 415

Phe Asp Gly Leu Gln Ile Ile Ser Val Tyr Ser Asn Lys Gly Ala Ser
                420                 425                 430

Ala Ala Ser Tyr Thr Ile Ser Leu Glu Ser Ser Thr Thr Gly Phe Thr
                435                 440                 445

Ala Asn Glu Ala Leu Val Glu Val Met Ser Cys Thr Thr Tyr Thr Thr
                450                 455                 460

Asp Gly Ser Gly Asn Leu Ala Val Thr Ile Ser Gly Gly Leu Pro Ala
465                 470                 475                 480

Val Phe Tyr Pro Lys Ala Gln Leu Ala Gly Ser Ile Cys Gly Glu
                485                 490                 495

<210> SEQ ID NO 2
<211> LENGTH: 43
<212> TYPE: PRT
<213> ORGANISM: Aspergillus niger

<400> SEQUENCE: 2

Thr Gly Gly Thr Thr Thr Thr Ala Thr Pro Thr Gly Ser Gly Ser Val
1               5                   10                  15

Thr Ser Thr Ser Lys Thr Thr Ala Thr Ala Ser Lys Thr Ser Thr Ser
                20                  25                  30

Thr Ser Ser Thr Ser Cys Thr Thr Pro Thr Ala
                35                  40

<210> SEQ ID NO 3
<211> LENGTH: 43
<212> TYPE: PRT
<213> ORGANISM: Bulgaria inquinans

<400> SEQUENCE: 3

Ser Gly Thr Ser Thr Gly Ser Trp Ser Ser Ser Ala Thr Ala Thr
1               5                   10                  15

Lys Thr Ser Thr Ser Ser Thr Ala Ser Lys Thr Ala Thr Thr Thr Thr
                20                  25                  30

Thr Ser Ser Thr Ala Cys Thr Ser Thr Ser Thr
                35                  40

<210> SEQ ID NO 4
<211> LENGTH: 102
<212> TYPE: PRT
<213> ORGANISM: Aspergillus niger

<400> SEQUENCE: 4

Val Ala Val Thr Phe Asp Leu Thr Ala Thr Thr Thr Tyr Gly Glu Asn
1               5                   10                  15

Ile Tyr Leu Val Gly Ser Ile Ser Gln Leu Gly Asp Trp Glu Thr Ser
                20                  25                  30
```

```
Asp Gly Ile Ala Leu Ser Ala Asp Lys Tyr Thr Ser Ser Asp Pro Leu
            35                  40                  45

Trp Tyr Val Thr Val Thr Leu Pro Ala Gly Glu Ser Phe Glu Tyr Lys
 50                  55                  60

Phe Ile Arg Ile Glu Ser Asp Ser Val Glu Trp Glu Ser Asp Pro
 65                  70                  75                  80

Asn Arg Glu Tyr Thr Val Pro Gln Ala Cys Gly Thr Ser Thr Ala Thr
                85                  90                  95

Val Thr Asp Thr Trp Arg
                100

<210> SEQ ID NO 5
<211> LENGTH: 101
<212> TYPE: PRT
<213> ORGANISM: Aspergillus ochraceus

<400> SEQUENCE: 5

Val Ala Val Thr Phe Glu Val Thr Ala Thr Val Tyr Gly Gln Asp
 1               5                  10                  15

Ile Lys Val Val Gly Ser Ile Ala Glu Leu Gly Ser Trp Ser Pro Ser
                20                  25                  30

Ser Ala Ile Ala Leu Ser Ala Asp Arg Tyr Thr Ser Ser Asn Pro Leu
            35                  40                  45

Trp Tyr Gly Thr Val Asn Val Pro Val Asp Lys Thr Phe Glu Tyr Lys
 50                  55                  60

Tyr Ile Arg Val Gln Asn Gly Ala Val Thr Trp Glu Ser Asp Pro Asn
 65                  70                  75                  80

Arg Ser Leu Ser Val Ala Gly Gly Cys Gly Val Ser Gly Lys Thr Gln
                85                  90                  95

Lys Asp Thr Trp Arg
                100

<210> SEQ ID NO 6
<211> LENGTH: 102
<212> TYPE: PRT
<213> ORGANISM: Penicillium sp.

<400> SEQUENCE: 6

Val Ala Val Thr Phe Asn Val Ile Ala Thr Thr Ala Tyr Gly Glu Asn
 1               5                  10                  15

Val Lys Leu Ala Gly Ser Ile Ser Gln Leu Gly Ser Trp Ser Thr Ser
                20                  25                  30

Ser Ala Ile Ala Leu Ser Ala Ser Ser Tyr Thr Ser Ser Asn His Leu
            35                  40                  45

Trp Phe Val Thr Ala Thr Leu Pro Ala Gly Thr Thr Phe Ser Tyr Lys
 50                  55                  60

Tyr Ile Arg Val Lys Ser Asp Gly Ser Ile Gln Trp Glu Ser Asp Pro
 65                  70                  75                  80

Asn Arg Ser Tyr Thr Val Pro Ala Val Cys Gly Thr Thr Ser Val Thr
                85                  90                  95

Ile Ser Asp Thr Trp Arg
                100

<210> SEQ ID NO 7
<211> LENGTH: 622
<212> TYPE: PRT
<213> ORGANISM: Artificial
```

<220> FEATURE:
<223> OTHER INFORMATION: Hybrid alpha-amylase

<400> SEQUENCE: 7

```
Leu Thr Pro Ala Gln Trp Arg Gly Gln Ser Ile Tyr Gln Val Leu Thr
 1               5                  10                  15

Asp Arg Phe Gly Arg Thr Asp Ser Thr Thr Ala Ala Cys Asp Val
             20                  25                  30

Asn Asp Tyr Cys Gly Gly Ser Trp Gln Gly Ile Ile Asn His Leu Asp
         35                  40                  45

Tyr Ile Gln Asp Met Gly Phe Ser Ala Ile Trp Ile Ser Pro Val Val
     50                  55                  60

Glu Asn Leu Val Gly Asp Thr Gln Asp Gly Ser Ala Tyr His Gly Tyr
 65                  70                  75                  80

Trp Ala Gln Asn Ile Tyr Ala Leu Asn Pro Asn Phe Gly Thr Val Ser
                 85                  90                  95

Asp Leu Val Ala Leu Ser Ala Ala Leu His Gln Arg Gly Met Tyr Leu
            100                 105                 110

Met Val Asp Val Val Thr Asn His Met Gly Tyr Asp Gly Cys Gly Asp
            115                 120                 125

Cys Val Asp Tyr Ser Val Phe Thr Pro Phe Asn Ser Gln Ser Tyr Phe
130                 135                 140

His Pro Phe Cys Leu Ile Asp Tyr Asn Asn Ser Thr Ser Ile Lys Val
145                 150                 155                 160

Cys Trp Glu Gly Asp Asn Ile Val Ser Leu Pro Asp Met Arg Thr Glu
                165                 170                 175

Asp Ser Asp Val Ala Thr Glu Trp Asn Thr Trp Ile Ser Glu Leu Val
            180                 185                 190

Ser Asn Tyr Ser Ile Asp Gly Leu Arg Ile Asp Ser Ala Gln Gln Val
        195                 200                 205

Asp Asn Ala Phe Phe Pro Pro Phe Gln Ala Ala Ala Gly Gly Ile His
    210                 215                 220

Val Leu Gly Glu Val Phe Asn Gly Asp Pro Asn Tyr Val Cys Pro Tyr
225                 230                 235                 240

Gln Asp Phe Met Ser Gly Val Leu Asn Tyr Pro Ala Tyr Tyr Tyr Ile
                245                 250                 255

Thr Gln Ala Phe Gln Ser Thr Ser Gly Ser Ile Ser Asn Leu Val Asn
            260                 265                 270

Gly Ile Asn Gln Met Lys Ser Thr Cys Thr Asp Thr Thr Leu Leu Gly
        275                 280                 285

Ser Phe Leu Glu Asn His Asp Asn Pro Arg Phe Pro Ser Tyr Thr Ser
    290                 295                 300

Asp Leu Ser Leu Asp Lys Asn Ala Ile Thr Phe Thr Ile Leu Gln Asp
305                 310                 315                 320

Gly Ile Pro Ile Ile Tyr Glu Gly Gln Glu Gln His Tyr Ser Gly Gly
                325                 330                 335

Thr Val Pro Asn Asn Arg Glu Ala Ile Trp Leu Ser Gly Tyr Asp Lys
            340                 345                 350

Ser Ala Pro Leu Tyr Thr Trp Ile Ala Ser Val Asn Gln Ile Arg Asn
        355                 360                 365

Gln Ala Ile Phe Lys Asp Ser Asn Tyr Leu Tyr Met Ala Trp Pro
    370                 375                 380

Ile Tyr Ser Asp Ala Ser Thr Ile Ala Met Arg Lys Gly Phe Asp Gly
385                 390                 395                 400
```

Leu Gln Ile Ile Ser Val Tyr Ser Asn Lys Gly Ala Ser Ala Ala Ser
                405                 410                 415

Tyr Thr Ile Ser Leu Glu Ser Ser Thr Thr Gly Phe Thr Ala Asn Glu
            420                 425                 430

Ala Leu Val Glu Val Met Ser Cys Thr Thr Tyr Thr Thr Asp Gly Ser
                435                 440                 445

Gly Asn Leu Ala Val Thr Ile Ser Gly Gly Leu Pro Ala Val Phe Tyr
            450                 455                 460

Pro Lys Ala Gln Leu Ala Gly Ser Gly Ile Cys Gly Glu Thr Gly Gly
465                 470                 475                 480

Thr Thr Thr Thr Ala Thr Pro Thr Gly Ser Gly Ser Val Thr Ser Thr
                485                 490                 495

Ser Lys Thr Thr Ala Thr Ala Ser Lys Thr Ser Thr Ser Thr Ser Ser
            500                 505                 510

Thr Ser Cys Thr Thr Pro Thr Ala Val Ala Val Thr Phe Asp Leu Thr
            515                 520                 525

Ala Thr Thr Thr Tyr Gly Glu Asn Ile Tyr Leu Val Gly Ser Ile Ser
            530                 535                 540

Gln Leu Gly Asp Trp Glu Thr Ser Asp Gly Ile Ala Leu Ser Ala Asp
545                 550                 555                 560

Lys Tyr Thr Ser Ser Asp Pro Leu Trp Tyr Val Thr Val Thr Leu Pro
                565                 570                 575

Ala Gly Glu Ser Phe Glu Tyr Lys Phe Ile Arg Ile Glu Ser Asp Asp
            580                 585                 590

Ser Val Glu Trp Glu Ser Asp Pro Asn Arg Glu Tyr Thr Val Pro Gln
                595                 600                 605

Ala Cys Gly Thr Ser Thr Ala Thr Val Thr Asp Thr Trp Arg
            610                 615                 620

<210> SEQ ID NO 8
<211> LENGTH: 619
<212> TYPE: PRT
<213> ORGANISM: Artificial
<220> FEATURE:
<223> OTHER INFORMATION: Hybrid alpha-amylase

<400> SEQUENCE: 8

Leu Thr Pro Ala Gln Trp Arg Gly Gln Ser Ile Tyr Gln Val Leu Thr
1               5                   10                  15

Asp Arg Phe Gly Arg Thr Asp Asp Ser Thr Thr Ala Ala Cys Asp Val
            20                  25                  30

Asn Asp Tyr Cys Gly Gly Ser Trp Gln Gly Ile Ile Asn His Leu Asp
        35                  40                  45

Tyr Ile Gln Asp Met Gly Phe Ser Ala Ile Trp Ile Ser Pro Val Val
    50                  55                  60

Glu Asn Leu Val Gly Asp Thr Gln Asp Gly Ser Ala Tyr His Gly Tyr
65                  70                  75                  80

Trp Ala Gln Asn Ile Tyr Ala Leu Asn Pro Asn Phe Gly Thr Val Ser
                85                  90                  95

Asp Leu Val Ala Leu Ser Ala Ala Leu His Gln Arg Gly Met Tyr Leu
            100                 105                 110

Met Val Asp Val Val Thr Asn His Met Gly Tyr Asp Gly Cys Gly Asp
        115                 120                 125

Cys Val Asp Tyr Ser Val Phe Thr Pro Phe Asn Ser Gln Ser Tyr Phe
    130                 135                 140

-continued

His Pro Phe Cys Leu Ile Asp Tyr Asn Asn Ser Thr Ser Ile Lys Val
145                 150                 155                 160

Cys Trp Glu Gly Asp Asn Ile Val Ser Leu Pro Asp Met Arg Thr Glu
            165                 170                 175

Asp Ser Asp Val Ala Thr Glu Trp Asn Thr Trp Ile Ser Glu Leu Val
        180                 185                 190

Ser Asn Tyr Ser Ile Asp Gly Leu Arg Ile Asp Ser Ala Gln Gln Val
    195                 200                 205

Asp Asn Ala Phe Phe Pro Pro Phe Gln Ala Ala Gly Gly Ile His
210                 215                 220

Val Leu Gly Glu Val Phe Asn Gly Asp Pro Asn Tyr Val Cys Pro Tyr
225                 230                 235                 240

Gln Asp Phe Met Ser Gly Val Leu Asn Tyr Pro Ala Tyr Tyr Ile
            245                 250                 255

Thr Gln Ala Phe Gln Ser Thr Ser Gly Ser Ile Ser Asn Leu Val Asn
            260                 265                 270

Gly Ile Asn Gln Met Lys Ser Thr Cys Thr Asp Thr Leu Leu Gly
        275                 280                 285

Ser Phe Leu Glu Asn His Asp Asn Pro Arg Phe Pro Ser Tyr Thr Ser
290                 295                 300

Asp Leu Ser Leu Asp Lys Asn Ala Ile Thr Phe Thr Ile Leu Gln Asp
305                 310                 315                 320

Gly Ile Pro Ile Ile Tyr Glu Gly Gln Glu Gln His Tyr Ser Gly Gly
                325                 330                 335

Thr Val Pro Asn Asn Arg Glu Ala Ile Trp Leu Ser Gly Tyr Asp Lys
            340                 345                 350

Ser Ala Pro Leu Tyr Thr Trp Ile Ala Ser Val Asn Gln Ile Arg Asn
        355                 360                 365

Gln Ala Ile Phe Lys Asp Ser Asn Tyr Leu Thr Tyr Met Ala Trp Pro
370                 375                 380

Ile Tyr Ser Asp Ala Ser Thr Ile Ala Met Arg Lys Gly Phe Asp Gly
385                 390                 395                 400

Leu Gln Ile Ile Ser Val Tyr Ser Asn Lys Gly Ala Ser Ala Ala Ser
                405                 410                 415

Tyr Thr Ile Ser Leu Glu Ser Ser Thr Thr Gly Phe Thr Ala Asn Glu
            420                 425                 430

Ala Leu Val Glu Val Met Ser Cys Thr Thr Tyr Thr Thr Asp Gly Ser
        435                 440                 445

Gly Asn Leu Ala Val Thr Ile Ser Gly Gly Leu Pro Ala Val Phe Tyr
450                 455                 460

Pro Lys Ala Gln Leu Ala Gly Ser Gly Ile Cys Ser Gly Thr Ser Thr
465                 470                 475                 480

Gly Ser Trp Ser Ser Ser Ser Ala Thr Ala Lys Thr Ser Thr Ser
            485                 490                 495

Ser Thr Ala Ser Lys Thr Ala Thr Thr Thr Thr Ser Ser Thr Ala
        500                 505                 510

Cys Thr Ser Thr Ser Thr Val Ala Val Thr Phe Glu Val Thr Ala Thr
        515                 520                 525

Thr Val Tyr Gly Gln Asp Ile Lys Val Val Gly Ser Ile Ala Glu Leu
    530                 535                 540

Gly Ser Trp Ser Pro Ser Ser Ala Ile Ala Leu Ser Ala Asp Arg Tyr
545                 550                 555                 560

```
Thr Ser Ser Asn Pro Leu Trp Tyr Gly Thr Val Asn Val Pro Val Asp
            565                 570                 575

Lys Thr Phe Glu Tyr Lys Tyr Ile Arg Val Gln Asn Gly Ala Val Thr
            580                 585                 590

Trp Glu Ser Asp Pro Asn Arg Ser Leu Ser Val Ala Gly Gly Cys Gly
            595                 600                 605

Val Ser Gly Lys Thr Gln Lys Asp Thr Trp Arg
            610                 615

<210> SEQ ID NO 9
<211> LENGTH: 620
<212> TYPE: PRT
<213> ORGANISM: Artificial
<220> FEATURE:
<223> OTHER INFORMATION: Hybrid alpha-amylase

<400> SEQUENCE: 9

Leu Thr Pro Ala Gln Trp Arg Gly Gln Ser Ile Tyr Gln Val Leu Thr
1               5                   10                  15

Asp Arg Phe Gly Arg Thr Asp Asp Ser Thr Thr Ala Ala Cys Asp Val
            20                  25                  30

Asn Asp Tyr Cys Gly Gly Ser Trp Gln Gly Ile Ile Asn His Leu Asp
            35                  40                  45

Tyr Ile Gln Asp Met Gly Phe Ser Ala Ile Trp Ile Ser Pro Val Val
    50                  55                  60

Glu Asn Leu Val Gly Asp Thr Gln Asp Gly Ser Ala Tyr His Gly Tyr
65                  70                  75                  80

Trp Ala Gln Asn Ile Tyr Ala Leu Asn Pro Asn Phe Gly Thr Val Ser
                85                  90                  95

Asp Leu Val Ala Leu Ser Ala Ala Leu His Gln Arg Gly Met Tyr Leu
            100                 105                 110

Met Val Asp Val Val Thr Asn His Met Gly Tyr Asp Gly Cys Gly Asp
            115                 120                 125

Cys Val Asp Tyr Ser Val Phe Thr Pro Phe Asn Ser Gln Ser Tyr Phe
130                 135                 140

His Pro Phe Cys Leu Ile Asp Tyr Asn Asn Ser Thr Ser Ile Lys Val
145                 150                 155                 160

Cys Trp Glu Gly Asp Asn Ile Val Ser Leu Pro Asp Met Arg Thr Glu
                165                 170                 175

Asp Ser Asp Val Ala Thr Glu Trp Asn Thr Trp Ile Ser Glu Leu Val
            180                 185                 190

Ser Asn Tyr Ser Ile Asp Gly Leu Arg Ile Asp Ser Ala Gln Gln Val
            195                 200                 205

Asp Asn Ala Phe Phe Pro Pro Phe Gln Ala Ala Ala Gly Gly Ile His
        210                 215                 220

Val Leu Gly Glu Val Phe Asn Gly Asp Pro Asn Tyr Val Cys Pro Tyr
225                 230                 235                 240

Gln Asp Phe Met Ser Gly Val Leu Asn Tyr Pro Ala Tyr Tyr Tyr Ile
                245                 250                 255

Thr Gln Ala Phe Gln Ser Thr Ser Gly Ser Ile Ser Asn Leu Val Asn
            260                 265                 270

Gly Ile Asn Gln Met Lys Ser Thr Cys Thr Asp Thr Thr Leu Leu Gly
        275                 280                 285

Ser Phe Leu Glu Asn His Asp Asn Pro Arg Phe Pro Ser Tyr Thr Ser
    290                 295                 300
```

```
Asp Leu Ser Leu Asp Lys Asn Ala Ile Thr Phe Thr Ile Leu Gln Asp
305                 310                 315                 320
Gly Ile Pro Ile Ile Tyr Glu Gly Gln Glu Gln His Tyr Ser Gly Gly
                325                 330                 335
Thr Val Pro Asn Asn Arg Glu Ala Ile Trp Leu Ser Gly Tyr Asp Lys
            340                 345                 350
Ser Ala Pro Leu Tyr Thr Trp Ile Ala Ser Val Asn Gln Ile Arg Asn
        355                 360                 365
Gln Ala Ile Phe Lys Asp Ser Asn Tyr Leu Thr Tyr Met Ala Trp Pro
370                 375                 380
Ile Tyr Ser Asp Ala Ser Thr Ile Ala Met Arg Lys Gly Phe Asp Gly
385                 390                 395                 400
Leu Gln Ile Ile Ser Val Tyr Ser Asn Lys Gly Ala Ser Ala Ala Ser
                405                 410                 415
Tyr Thr Ile Ser Leu Glu Ser Ser Thr Thr Gly Phe Thr Ala Asn Glu
            420                 425                 430
Ala Leu Val Glu Val Met Ser Cys Thr Thr Tyr Thr Thr Asp Gly Ser
        435                 440                 445
Gly Asn Leu Ala Val Thr Ile Ser Gly Gly Leu Pro Ala Val Phe Tyr
450                 455                 460
Pro Lys Ala Gln Leu Ala Gly Ser Gly Ile Cys Thr Gly Gly Thr Thr
465                 470                 475                 480
Thr Thr Ala Thr Pro Thr Gly Ser Gly Ser Val Thr Ser Thr Ser Lys
                485                 490                 495
Thr Thr Ala Thr Ala Ser Lys Thr Ser Thr Thr Ser Ser Thr Ser
            500                 505                 510
Cys Thr Thr Pro Thr Ala Val Ala Val Thr Phe Asn Val Ile Ala Thr
        515                 520                 525
Thr Ala Tyr Gly Glu Asn Val Lys Leu Ala Gly Ser Ile Ser Gln Leu
530                 535                 540
Gly Ser Trp Ser Thr Ser Ser Ala Ile Ala Leu Ser Ala Ser Ser Tyr
545                 550                 555                 560
Thr Ser Ser Asn His Leu Trp Phe Val Thr Ala Thr Leu Pro Ala Gly
                565                 570                 575
Thr Thr Phe Ser Tyr Lys Tyr Ile Arg Val Lys Ser Asp Gly Ser Ile
            580                 585                 590
Gln Trp Glu Ser Asp Pro Asn Arg Ser Tyr Thr Val Pro Ala Val Cys
        595                 600                 605
Gly Thr Thr Ser Val Thr Ile Ser Asp Thr Trp Arg
610                 615                 620

<210> SEQ ID NO 10
<211> LENGTH: 1769
<212> TYPE: DNA
<213> ORGANISM: Acidomyces acidothermus

<400> SEQUENCE: 10
atgaggtcct tcagtgcttt cctgcctttg cttctatga tcactgctac ctttgctcta      60
actcctgctc aatggcgtgg tcaatccata tatcaagtcc taactgaccg ctttggacgt     120
actgatgatt cgaccacagc agcttgtgat gttaatgact attgtggtgg atcatggcag     180
ggtatcatca atcatcttga ttatatccag gatatgggat tcagtgcggt gagttaccag     240
attcggctat cttgcatttg caggcagagt cggttgctga gtatcttata gatctggata     300
tctccagtgg tggagaacct ggttggggac actcaagatg gatccgccta tcatggctac     360
```

```
tgggctcaga acatatatgc tctcaacccc aattttggaa cggtttcgga tctcgtggcc    420
ctttctgctg ctcttcatca gcgcggaatg gtaattctaa aattctaaag actaaatgga    480
gaattgctaa ttagagacag taccttatgg tggatgtggt gacaaaccat atgggatatg    540
atggctgcgg ggattgtgta gactacagtg tcttcacacc gttcaactct gtgagcctag    600
tttcatacga tcttcgccat ccaattgtct cacactcaat gggtagagac taacgttttc    660
agcaatccta tttccatccc ttctgtctca ttgactacaa caattcgacc agcatcaaag    720
tggtaagtaa catccactct gttctagtgc catgctgaga ttgtacagtg ctgggaggga    780
gacaacattg tatctcttcc tgatatgaga actgaagatt cagacgtggc aaccgagtgg    840
aatacctgga tttcagaatt ggtttcgaat tacagcattg acgggctacg gattgacagt    900
gctcagcaag tcgacaacgc cttctttcca ccgtttcaag cagctgcggg aggaattcat    960
gtccttggag aagtcttcaa tggtgatccg aattatgtct gcccctatca agactttatg   1020
agtggagttt tgaactatcc agcgtgagga tctatatatc attgcacaga atactttcta   1080
atatcttcag ttactactac atcacccaag ccttccaatc taccagtggt agcatcagca   1140
acctggttaa tggcatcaac caatgaagag cacctgcac agacaccacc cttctcggat   1200
ccttcctcga aaccatgaca accccccgct tcccatccta cacctcggat ctctctctgg   1260
acaagaacgc catcaccttc accatcctcc aagacggcat ccccatcatc tacgaaggcc   1320
aagaacagca ctactcgggt ggcactgtcc ctaacaaccg agaagccatc tggctctccg   1380
gctatgacaa gtctgccccg ctctacacct ggattgcatc cgtgaaccag attagaaatc   1440
aggctatctt taaggatagc aactatctga cctacatggc ttggcctatc tattcagacg   1500
catcgaccat tgccatgcgg aaggggtttg acggccttca gatcatcagt gtctactcaa   1560
ataaaggtgc cagtgcagcc agctataccatctcccttga atcgagtact actggcttca   1620
cggctaacga ggcgctggtc gaggtcatga gttgtacgac ctatactacg gatgggagtg   1680
gtaacttagc tgtgactatc tctggcgggt tgccggccgt gttctatcct aaggctcagt   1740
tggctgggag tggaatatgt ggggagtaa                                     1769
```

<210> SEQ ID NO 11
<211> LENGTH: 556
<212> TYPE: PRT
<213> ORGANISM: Trametes cingulata

<400> SEQUENCE: 11

```
Gln Ser Ser Ala Ala Asp Ala Tyr Val Ala Ser Glu Ser Pro Ile Ala
1               5                   10                  15

Lys Ala Gly Val Leu Ala Asn Ile Gly Pro Ser Gly Ser Lys Ser Asn
                20                  25                  30

Gly Ala Lys Ala Gly Ile Val Ile Ala Ser Pro Ser Thr Ser Asn Pro
            35                  40                  45

Asn Tyr Leu Tyr Thr Trp Thr Arg Asp Ser Ser Leu Val Phe Lys Ala
        50                  55                  60

Leu Ile Asp Gln Phe Thr Thr Gly Glu Asp Thr Ser Leu Arg Thr Leu
65                  70                  75                  80

Ile Asp Glu Phe Thr Ser Ala Glu Ala Ile Leu Gln Gln Val Pro Asn
                85                  90                  95

Pro Ser Gly Thr Val Ser Thr Gly Gly Leu Gly Glu Pro Lys Phe Asn
                100                 105                 110

Ile Asp Glu Thr Ala Phe Thr Asp Ala Trp Gly Arg Pro Gln Arg Asp
```

```
            115                 120                 125
Gly Pro Ala Leu Arg Ala Thr Ala Ile Ile Thr Tyr Ala Asn Trp Leu
    130                 135                 140

Leu Asp Asn Lys Asn Thr Thr Tyr Val Thr Asn Thr Leu Trp Pro Ile
145                 150                 155                 160

Ile Lys Leu Asp Leu Asp Tyr Val Ala Ser Asn Trp Asn Gln Ser Thr
                165                 170                 175

Phe Asp Leu Trp Glu Glu Ile Asn Ser Ser Ser Phe Phe Thr Thr Ala
            180                 185                 190

Val Gln His Arg Ala Leu Arg Glu Gly Ala Thr Phe Ala Asn Arg Ile
        195                 200                 205

Gly Gln Thr Ser Val Val Ser Gly Tyr Thr Thr Gln Ala Asn Asn Leu
    210                 215                 220

Leu Cys Phe Leu Gln Ser Tyr Trp Asn Pro Thr Gly Gly Tyr Ile Thr
225                 230                 235                 240

Ala Asn Thr Gly Gly Gly Arg Ser Gly Lys Asp Ala Asn Thr Val Leu
                245                 250                 255

Thr Ser Ile His Thr Phe Asp Pro Ala Ala Gly Cys Asp Ala Val Thr
            260                 265                 270

Phe Gln Pro Cys Ser Asp Lys Ala Leu Ser Asn Leu Lys Val Tyr Val
        275                 280                 285

Asp Ala Phe Arg Ser Ile Tyr Ser Ile Asn Ser Gly Ile Ala Ser Asn
    290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335

Ala Leu Ile Val Trp Asn Lys Leu Gly Ala Leu Asn Val Thr Ser Thr
            340                 345                 350

Ser Leu Pro Phe Phe Gln Gln Phe Ser Ser Gly Val Thr Val Gly Thr
        355                 360                 365

Tyr Ala Ser Ser Ser Ser Thr Phe Lys Thr Leu Thr Ser Ala Ile Lys
    370                 375                 380

Thr Phe Ala Asp Gly Phe Leu Ala Val Asn Ala Lys Tyr Thr Pro Ser
385                 390                 395                 400

Asn Gly Gly Leu Ala Glu Gln Tyr Ser Arg Ser Asn Gly Ser Pro Val
                405                 410                 415

Ser Ala Val Asp Leu Thr Trp Ser Tyr Ala Ala Ala Leu Thr Ser Phe
            420                 425                 430

Ala Ala Arg Ser Gly Lys Thr Tyr Ala Ser Trp Gly Ala Ala Gly Leu
        435                 440                 445

Thr Val Pro Thr Thr Cys Ser Gly Gly Gly Ala Gly Thr Val Ala
    450                 455                 460

Val Thr Phe Asn Val Gln Ala Thr Thr Val Phe Gly Glu Asn Ile Tyr
465                 470                 475                 480

Ile Thr Gly Ser Val Pro Ala Leu Gln Asn Trp Ser Pro Asp Asn Ala
                485                 490                 495

Leu Ile Leu Ser Ala Ala Asn Tyr Pro Thr Trp Ser Ile Thr Val Asn
            500                 505                 510

Leu Pro Ala Ser Thr Thr Ile Glu Tyr Lys Tyr Ile Arg Lys Phe Asn
        515                 520                 525

Gly Ala Val Thr Trp Glu Ser Asp Pro Asn Asn Ser Ile Thr Thr Pro
    530                 535                 540
```

Ala Ser Gly Thr Phe Thr Gln Asn Asp Thr Trp Arg
545                 550                 555

<210> SEQ ID NO 12
<211> LENGTH: 591
<212> TYPE: PRT
<213> ORGANISM: Talaromyces emersonii

<400> SEQUENCE: 12

Ala Thr Gly Ser Leu Asp Ser Phe Leu Ala Thr Glu Thr Pro Ile Ala
1               5                   10                  15

Leu Gln Gly Val Leu Asn Asn Ile Gly Pro Asn Gly Ala Asp Val Ala
            20                  25                  30

Gly Ala Ser Ala Gly Ile Val Val Ala Ser Pro Ser Arg Ser Asp Pro
        35                  40                  45

Asn Tyr Phe Tyr Ser Trp Thr Arg Asp Ala Ala Leu Thr Ala Lys Tyr
    50                  55                  60

Leu Val Asp Ala Phe Ile Ala Gly Asn Lys Asp Leu Glu Gln Thr Ile
65                  70                  75                  80

Gln Gln Tyr Ile Ser Ala Gln Ala Lys Val Gln Thr Ile Ser Asn Pro
                85                  90                  95

Ser Gly Asp Leu Ser Thr Gly Gly Leu Gly Glu Pro Lys Phe Asn Val
            100                 105                 110

Asn Glu Thr Ala Phe Thr Gly Pro Trp Gly Arg Pro Gln Arg Asp Gly
        115                 120                 125

Pro Ala Leu Arg Ala Thr Ala Leu Ile Ala Tyr Ala Asn Tyr Leu Ile
130                 135                 140

Asp Asn Gly Glu Ala Ser Thr Ala Asp Glu Ile Ile Trp Pro Ile Val
145                 150                 155                 160

Gln Asn Asp Leu Ser Tyr Ile Thr Gln Tyr Trp Asn Ser Ser Thr Phe
                165                 170                 175

Asp Leu Trp Glu Glu Val Glu Gly Ser Ser Phe Phe Thr Thr Ala Val
            180                 185                 190

Gln His Arg Ala Leu Val Glu Gly Asn Ala Leu Ala Thr Arg Leu Asn
        195                 200                 205

His Thr Cys Ser Asn Cys Val Ser Gln Ala Pro Gln Val Leu Cys Phe
210                 215                 220

Leu Gln Ser Tyr Trp Thr Gly Ser Tyr Val Leu Ala Asn Phe Gly Gly
225                 230                 235                 240

Ser Gly Arg Ser Gly Lys Asp Val Asn Ser Ile Leu Gly Ser Ile His
                245                 250                 255

Thr Phe Asp Pro Ala Gly Gly Cys Asp Asp Ser Thr Phe Gln Pro Cys
            260                 265                 270

Ser Ala Arg Ala Leu Ala Asn His Lys Val Val Thr Asp Ser Phe Arg
        275                 280                 285

Ser Ile Tyr Ala Ile Asn Ser Gly Ile Ala Glu Gly Ser Ala Val Ala
    290                 295                 300

Val Gly Arg Tyr Pro Glu Asp Val Tyr Gln Gly Gly Asn Pro Trp Tyr
305                 310                 315                 320

Leu Ala Thr Ala Ala Ala Glu Gln Leu Tyr Asp Ala Ile Tyr Gln
                325                 330                 335

Trp Lys Lys Ile Gly Ser Ile Ser Ile Thr Asp Val Ser Leu Pro Phe
            340                 345                 350

Phe Gln Asp Ile Tyr Pro Ser Ala Ala Val Gly Thr Tyr Asn Ser Gly

```
                355                 360                 365
Ser Thr Thr Phe Asn Asp Ile Ile Ser Ala Val Gln Thr Tyr Gly Asp
370                 375                 380

Gly Tyr Leu Ser Ile Val Glu Lys Tyr Thr Pro Ser Asp Gly Ser Leu
385                 390                 395                 400

Thr Glu Gln Phe Ser Arg Thr Asp Gly Thr Pro Leu Ser Ala Ser Ala
                405                 410                 415

Leu Thr Trp Ser Tyr Ala Ser Leu Leu Thr Ala Ser Ala Arg Arg Gln
                420                 425                 430

Ser Val Val Pro Ala Ser Trp Gly Glu Ser Ala Ser Ser Val Pro
            435                 440                 445

Ala Val Cys Ser Ala Thr Ser Ala Thr Gly Pro Tyr Ser Thr Ala Thr
            450                 455                 460

Asn Thr Val Trp Pro Ser Ser Gly Ser Gly Ser Ser Thr Thr Thr Ser
465                 470                 475                 480

Ser Ala Pro Cys Thr Thr Pro Thr Ser Val Ala Val Thr Phe Asp Glu
                485                 490                 495

Ile Val Ser Thr Ser Tyr Gly Glu Thr Ile Tyr Leu Ala Gly Ser Ile
                500                 505                 510

Pro Glu Leu Gly Asn Trp Ser Thr Ala Ser Ala Ile Pro Leu Arg Ala
            515                 520                 525

Asp Ala Tyr Thr Asn Ser Asn Pro Leu Trp Tyr Val Thr Val Asn Leu
            530                 535                 540

Pro Pro Gly Thr Ser Phe Glu Tyr Lys Phe Lys Asn Gln Thr Asp
545                 550                 555                 560

Gly Thr Ile Val Trp Glu Asp Pro Asn Arg Ser Tyr Thr Val Pro
                565                 570                 575

Ala Tyr Cys Gly Gln Thr Thr Ala Ile Leu Asp Asp Ser Trp Gln
            580                 585                 590

<210> SEQ ID NO 13
<211> LENGTH: 555
<212> TYPE: PRT
<213> ORGANISM: Pycnoporus sanguineus

<400> SEQUENCE: 13

Gln Ser Ser Ala Val Asp Ala Tyr Val Ala Ser Glu Ser Pro Ile Ala
1               5                   10                  15

Lys Gln Gly Val Leu Asn Asn Ile Gly Pro Asn Gly Ser Lys Ala His
                20                  25                  30

Gly Ala Lys Ala Gly Ile Val Val Ala Ser Pro Ser Thr Glu Asn Pro
            35                  40                  45

Asp Tyr Leu Tyr Thr Trp Thr Arg Asp Ser Ser Leu Val Phe Lys Leu
50                  55                  60

Leu Ile Asp Gln Phe Thr Ser Gly Asp Thr Ser Leu Arg Gly Leu
65                  70                  75                  80

Ile Asp Asp Phe Thr Ser Ala Glu Ala Ile Leu Gln Gln Val Ser Asn
                85                  90                  95

Pro Ser Gly Thr Val Ser Thr Gly Gly Leu Gly Glu Pro Lys Phe Asn
                100                 105                 110

Ile Asp Glu Thr Ala Phe Thr Gly Ala Trp Gly Arg Pro Gln Arg Asp
            115                 120                 125

Gly Pro Ala Leu Arg Ala Thr Ser Ile Ile Arg Tyr Ala Asn Trp Leu
    130                 135                 140
```

-continued

Leu Asp Asn Gly Asn Thr Thr Tyr Val Ser Asn Thr Leu Trp Pro Val
145                 150                 155                 160

Ile Gln Leu Asp Leu Asp Tyr Val Ala Asp Asn Trp Asn Gln Ser Thr
            165                 170                 175

Phe Asp Leu Trp Glu Glu Val Asp Ser Ser Phe Thr Thr Ala
                180                 185                 190

Val Gln His Arg Ala Leu Arg Glu Gly Ala Thr Phe Ala Ser Arg Ile
            195                 200                 205

Gly Gln Ser Ser Val Val Ser Gly Tyr Thr Thr Gln Ala Asp Asn Leu
            210                 215                 220

Leu Cys Phe Leu Gln Ser Tyr Trp Asn Pro Ser Gly Gly Tyr Val Thr
225                 230                 235                 240

Ala Asn Thr Gly Gly Gly Arg Ser Gly Lys Asp Ser Asn Thr Val Leu
            245                 250                 255

Thr Ser Ile His Thr Phe Asp Pro Ala Ala Gly Cys Asp Ala Ala Thr
            260                 265                 270

Phe Gln Pro Cys Ser Asp Lys Ala Leu Ser Asn Leu Lys Val Tyr Val
            275                 280                 285

Asp Ala Phe Arg Ser Ile Tyr Thr Ile Asn Asn Gly Ile Ala Ser Asn
290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
            325                 330                 335

Ala Leu Tyr Val Trp Asp Gln Leu Gly Gly Leu Asn Val Thr Ser Thr
            340                 345                 350

Ser Leu Ala Phe Phe Gln Gln Phe Ala Ser Gly Leu Ser Thr Gly Thr
            355                 360                 365

Tyr Ser Ala Ser Ser Ser Thr Tyr Ala Thr Leu Thr Ser Ala Ile Arg
            370                 375                 380

Ser Phe Ala Asp Gly Phe Leu Ala Ile Asn Ala Lys Tyr Thr Pro Ala
385                 390                 395                 400

Asp Gly Gly Leu Ala Glu Gln Tyr Ser Arg Asn Asp Gly Thr Pro Leu
            405                 410                 415

Ser Ala Val Asp Leu Thr Trp Ser Tyr Ala Ala Ala Leu Thr Ala Phe
            420                 425                 430

Ala Ala Arg Glu Gly Lys Thr Tyr Gly Ser Trp Gly Ala Ala Gly Leu
            435                 440                 445

Thr Val Pro Ala Ser Cys Ser Gly Gly Gly Ala Thr Val Ala Val
450                 455                 460

Thr Phe Asn Val Gln Ala Thr Thr Val Phe Gly Glu Asn Ile Tyr Ile
465                 470                 475                 480

Thr Gly Ser Val Ala Ala Leu Gln Asn Trp Ser Pro Asp Asn Ala Leu
            485                 490                 495

Ile Leu Ser Ala Ala Asn Tyr Pro Thr Trp Ser Ile Thr Val Asn Leu
            500                 505                 510

Pro Ala Asn Thr Val Val Gln Tyr Lys Tyr Ile Arg Lys Phe Asn Gly
            515                 520                 525

Gln Val Thr Trp Glu Ser Asp Pro Asn Asn Gln Ile Thr Thr Pro Ser
            530                 535                 540

Gly Gly Ser Phe Thr Gln Asn Asp Val Trp Arg
545                 550                 555

<210> SEQ ID NO 14
<211> LENGTH: 556
<212> TYPE: PRT
<213> ORGANISM: Gloeophyllum sepiarium

<400> SEQUENCE: 14

| | | | | | | | | | | | | | | | |
|---|---|---|---|---|---|---|---|---|---|---|---|---|---|---|---|
| Gln | Ser | Val | Asp | Ser | Tyr | Val | Ser | Ser | Glu | Gly | Pro | Ile | Ala | Lys | Ala |
| 1 | | | | 5 | | | | | 10 | | | | | 15 | |
| Gly | Val | Leu | Ala | Asn | Ile | Gly | Pro | Asn | Gly | Ser | Lys | Ala | Ser | Gly | Ala |
| | | | 20 | | | | | 25 | | | | | 30 | | |
| Ser | Ala | Gly | Val | Val | Ala | Ser | Pro | Ser | Thr | Ser | Asp | Pro | Asp | Tyr | |
| | | | 35 | | | | 40 | | | | | 45 | | | |
| Trp | Tyr | Thr | Trp | Thr | Arg | Asp | Ser | Ser | Leu | Val | Phe | Lys | Ser | Leu | Ile |
| | 50 | | | | | 55 | | | | | 60 | | | | |
| Asp | Gln | Tyr | Thr | Thr | Gly | Ile | Asp | Ser | Thr | Ser | Ser | Leu | Arg | Thr | Leu |
| 65 | | | | | 70 | | | | | 75 | | | | | 80 |
| Ile | Asp | Asp | Phe | Val | Thr | Ala | Glu | Ala | Asn | Leu | Gln | Gln | Val | Ser | Asn |
| | | | | 85 | | | | | 90 | | | | | 95 | |
| Pro | Ser | Gly | Thr | Leu | Thr | Thr | Gly | Gly | Leu | Gly | Glu | Pro | Lys | Phe | Asn |
| | | | 100 | | | | | 105 | | | | | 110 | | |
| Val | Asp | Glu | Thr | Ala | Phe | Thr | Gly | Ala | Trp | Gly | Arg | Pro | Gln | Arg | Asp |
| | | | 115 | | | | 120 | | | | | 125 | | | |
| Gly | Pro | Ala | Leu | Arg | Ser | Thr | Ala | Leu | Ile | Thr | Tyr | Gly | Asn | Trp | Leu |
| | 130 | | | | | 135 | | | | | 140 | | | | |
| Leu | Ser | Asn | Gly | Asn | Thr | Ser | Tyr | Val | Thr | Ser | Asn | Leu | Trp | Pro | Ile |
| 145 | | | | | 150 | | | | | 155 | | | | | 160 |
| Ile | Gln | Asn | Asp | Leu | Gly | Tyr | Val | Val | Ser | Tyr | Trp | Asn | Gln | Ser | Thr |
| | | | | 165 | | | | | 170 | | | | | 175 | |
| Tyr | Asp | Leu | Trp | Glu | Glu | Val | Asp | Ser | Ser | Ser | Phe | Phe | Thr | Thr | Ala |
| | | | 180 | | | | | 185 | | | | | 190 | | |
| Val | Gln | His | Arg | Ala | Leu | Arg | Glu | Gly | Ala | Ala | Phe | Ala | Thr | Ala | Ile |
| | | | 195 | | | | | 200 | | | | | 205 | | |
| Gly | Gln | Thr | Ser | Gln | Val | Ser | Ser | Tyr | Thr | Thr | Gln | Ala | Asp | Asn | Leu |
| | 210 | | | | | 215 | | | | | 220 | | | | |
| Leu | Cys | Phe | Leu | Gln | Ser | Tyr | Trp | Asn | Pro | Ser | Gly | Gly | Tyr | Ile | Thr |
| 225 | | | | | 230 | | | | | 235 | | | | | 240 |
| Ala | Asn | Thr | Gly | Gly | Gly | Arg | Ser | Gly | Lys | Asp | Ala | Asn | Thr | Leu | Leu |
| | | | | 245 | | | | | 250 | | | | | 255 | |
| Ala | Ser | Ile | His | Thr | Tyr | Asp | Pro | Ser | Ala | Gly | Cys | Asp | Ala | Ala | Thr |
| | | | 260 | | | | | 265 | | | | | 270 | | |
| Phe | Gln | Pro | Cys | Ser | Asp | Lys | Ala | Leu | Ser | Asn | Leu | Lys | Val | Tyr | Val |
| | | | 275 | | | | | 280 | | | | | 285 | | |
| Asp | Ser | Phe | Arg | Ser | Val | Tyr | Ser | Ile | Asn | Ser | Gly | Val | Ala | Ser | Asn |
| | 290 | | | | | 295 | | | | | 300 | | | | |
| Ala | Ala | Val | Ala | Thr | Gly | Arg | Tyr | Pro | Glu | Asp | Ser | Tyr | Gln | Gly | Gly |
| 305 | | | | | 310 | | | | | 315 | | | | | 320 |
| Asn | Pro | Trp | Tyr | Leu | Thr | Thr | Phe | Ala | Val | Ala | Glu | Gln | Leu | Tyr | Asp |
| | | | | 325 | | | | | 330 | | | | | 335 | |
| Ala | Leu | Asn | Val | Trp | Glu | Ser | Gln | Gly | Ser | Leu | Glu | Val | Thr | Ser | Thr |
| | | | 340 | | | | | 345 | | | | | 350 | | |
| Ser | Leu | Ala | Phe | Phe | Gln | Gln | Phe | Ser | Ser | Gly | Val | Thr | Ala | Gly | Thr |
| | | | 355 | | | | | 360 | | | | | 365 | | |
| Tyr | Ser | Ser | Ser | Ser | Thr | Tyr | Ser | Thr | Leu | Thr | Ser | Ala | Ile | Lys | |
| | 370 | | | | | 375 | | | | | 380 | | | | |

```
Asn Phe Ala Asp Gly Phe Val Ala Ile Asn Ala Lys Tyr Thr Pro Ser
385                 390                 395                 400

Asn Gly Gly Leu Ala Glu Gln Tyr Ser Lys Ser Asp Gly Ser Pro Leu
            405                 410                 415

Ser Ala Val Asp Leu Thr Trp Ser Tyr Ala Ser Ala Leu Thr Ala Phe
            420                 425                 430

Glu Ala Arg Asn Asn Thr Gln Phe Ala Gly Trp Gly Ala Ala Gly Leu
            435                 440                 445

Thr Val Pro Ser Ser Cys Ser Gly Asn Ser Gly Pro Thr Val Ala
    450                 455                 460

Val Thr Phe Asn Val Asn Ala Glu Thr Val Trp Gly Glu Asn Ile Tyr
465                 470                 475                 480

Leu Thr Gly Ser Val Asp Ala Leu Glu Asn Trp Ser Ala Asp Asn Ala
            485                 490                 495

Leu Leu Leu Ser Ser Ala Asn Tyr Pro Thr Trp Ser Ile Thr Val Asn
            500                 505                 510

Leu Pro Ala Ser Thr Ala Ile Glu Tyr Lys Tyr Ile Arg Lys Asn Asn
            515                 520                 525

Gly Ala Val Thr Trp Glu Ser Asp Pro Asn Asn Ser Ile Thr Thr Pro
530                 535                 540

Ala Ser Gly Ser Thr Thr Glu Asn Asp Thr Trp Arg
545                 550                 555

<210> SEQ ID NO 15
<211> LENGTH: 559
<212> TYPE: PRT
<213> ORGANISM: Gloeophyllum trabeum

<400> SEQUENCE: 15

Gln Ser Val Asp Ser Tyr Val Gly Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ala Ala Gly Val Val Val Ala Ser Pro Ser Lys Ser Asp Pro Asp Tyr
            35                  40                  45

Trp Tyr Thr Trp Thr Arg Asp Ser Ser Leu Val Phe Lys Ser Leu Ile
50                  55                  60

Asp Gln Tyr Thr Thr Gly Ile Asp Ser Thr Ser Ser Leu Arg Ser Leu
65                  70                  75                  80

Ile Asp Ser Phe Val Ile Ala Glu Ala Asn Ile Gln Gln Val Ser Asn
                85                  90                  95

Pro Ser Gly Thr Leu Thr Thr Gly Gly Leu Gly Glu Pro Lys Phe Asn
            100                 105                 110

Val Asp Glu Thr Ala Phe Thr Gly Ala Trp Gly Arg Pro Gln Arg Asp
            115                 120                 125

Gly Pro Ala Leu Arg Ala Thr Ala Leu Ile Thr Tyr Gly Asn Trp Leu
            130                 135                 140

Leu Ser Asn Gly Asn Thr Thr Trp Val Thr Ser Thr Leu Trp Pro Ile
145                 150                 155                 160

Ile Gln Asn Asp Leu Asn Tyr Val Val Gln Tyr Trp Asn Gln Thr Thr
                165                 170                 175

Phe Asp Leu Trp Glu Glu Val Asn Ser Ser Phe Phe Thr Thr Ala
            180                 185                 190

Val Gln His Arg Ala Leu Arg Glu Gly Ala Ala Phe Ala Thr Lys Ile
            195                 200                 205
```

```
Gly Gln Thr Ser Ser Val Ser Ser Tyr Thr Gln Ala Ala Asn Leu
    210                 215                 220

Leu Cys Phe Leu Gln Ser Tyr Trp Asn Pro Thr Ser Gly Tyr Ile Thr
225                 230                 235                 240

Ala Asn Thr Gly Gly Arg Ser Gly Lys Asp Ala Asn Thr Leu Leu
                245                 250                 255

Ala Ser Ile His Thr Tyr Asp Pro Ser Ala Gly Cys Asp Ala Thr Thr
                260                 265                 270

Phe Gln Pro Cys Ser Asp Lys Ala Leu Ser Asn Leu Lys Val Tyr Val
            275                 280                 285

Asp Ser Phe Arg Ser Val Tyr Ser Ile Asn Ser Gly Ile Ala Ser Asn
        290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Ala Ala Gln Gly Ser Leu Asn Val Thr Ser Ile
                340                 345                 350

Ser Leu Pro Phe Phe Gln Gln Phe Ser Ser Ser Val Thr Ala Gly Thr
            355                 360                 365

Tyr Ala Ser Ser Ser Thr Thr Tyr Thr Thr Leu Thr Ser Ala Ile Lys
370                 375                 380

Ser Phe Ala Asp Gly Phe Val Ala Ile Asn Ala Gln Tyr Thr Pro Ser
385                 390                 395                 400

Asn Gly Gly Leu Ala Glu Gln Phe Ser Arg Ser Asn Gly Ala Pro Val
                405                 410                 415

Ser Ala Val Asp Leu Thr Trp Ser Tyr Ala Ser Ala Leu Thr Ala Phe
            420                 425                 430

Glu Ala Arg Asn Asn Thr Gln Phe Ala Gly Trp Gly Ala Val Gly Leu
                435                 440                 445

Thr Val Pro Thr Ser Cys Ser Ser Asn Ser Gly Gly Gly Gly Gly Ser
    450                 455                 460

Thr Val Ala Val Thr Phe Asn Val Asn Ala Gln Thr Val Trp Gly Glu
465                 470                 475                 480

Asn Ile Tyr Ile Thr Gly Ser Val Asp Ala Leu Ser Asn Trp Ser Pro
                485                 490                 495

Asp Asn Ala Leu Leu Leu Ser Ala Asn Tyr Pro Thr Trp Ser Ile
            500                 505                 510

Thr Val Asn Leu Pro Ala Ser Thr Ala Ile Gln Tyr Lys Tyr Ile Arg
        515                 520                 525

Lys Asn Asn Gly Ala Val Thr Trp Glu Ser Asp Pro Asn Asn Ser Ile
    530                 535                 540

Thr Thr Pro Ala Ser Gly Ser Val Thr Glu Asn Asp Thr Trp Arg
545                 550                 555

<210> SEQ ID NO 16
<211> LENGTH: 515
<212> TYPE: PRT
<213> ORGANISM: Bacillus steaothermophillus

<400> SEQUENCE: 16

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
```

```
            20                  25                  30
Leu Ser Ser Leu Gly Ile Thr Ala Leu Trp Leu Pro Pro Ala Tyr Lys
         35                  40                  45
Gly Thr Ser Arg Ser Asp Val Gly Tyr Gly Val Tyr Asp Leu Tyr Asp
     50                  55                  60
Leu Gly Glu Phe Asn Gln Lys Gly Thr Val Arg Thr Lys Tyr Gly Thr
 65                  70                  75                  80
Lys Ala Gln Tyr Leu Gln Ala Ile Gln Ala His Ala Ala Gly Met
                 85                  90                  95
Gln Val Tyr Ala Asp Val Phe Asp His Lys Gly Ala Asp Gly
             100                 105                 110
Thr Glu Trp Val Asp Ala Val Glu Val Asn Pro Ser Asp Arg Asn Gln
             115                 120                 125
Glu Ile Ser Gly Thr Tyr Gln Ile Gln Ala Trp Thr Lys Phe Asp Phe
             130                 135                 140
Pro Gly Arg Gly Asn Thr Tyr Ser Ser Phe Lys Trp Arg Trp Tyr His
145                 150                 155                 160
Phe Asp Gly Val Asp Trp Asp Glu Ser Arg Lys Leu Ser Arg Ile Tyr
                 165                 170                 175
Lys Phe Arg Gly Ile Gly Lys Ala Trp Asp Trp Glu Val Asp Thr Glu
                 180                 185                 190
Asn Gly Asn Tyr Asp Tyr Leu Met Tyr Ala Asp Leu Asp Met Asp His
                 195                 200                 205
Pro Glu Val Val Thr Glu Leu Lys Asn Trp Gly Lys Trp Tyr Val Asn
             210                 215                 220
Thr Thr Asn Ile Asp Gly Phe Arg Leu Asp Ala Val Lys His Ile Lys
225                 230                 235                 240
Phe Ser Phe Phe Pro Asp Trp Leu Ser Tyr Val Arg Ser Gln Thr Gly
                 245                 250                 255
Lys Pro Leu Phe Thr Val Gly Glu Tyr Trp Ser Tyr Asp Ile Asn Lys
                 260                 265                 270
Leu His Asn Tyr Ile Thr Lys Thr Asn Gly Thr Met Ser Leu Phe Asp
                 275                 280                 285
Ala Pro Leu His Asn Lys Phe Tyr Thr Ala Ser Lys Ser Gly Gly Ala
             290                 295                 300
Phe Asp Met Arg Thr Leu Met Thr Asn Thr Leu Met Lys Asp Gln Pro
305                 310                 315                 320
Thr Leu Ala Val Thr Phe Val Asp Asn His Asp Thr Glu Pro Gly Gln
                 325                 330                 335
Ala Leu Gln Ser Trp Val Asp Pro Trp Phe Lys Pro Leu Ala Tyr Ala
             340                 345                 350
Phe Ile Leu Thr Arg Gln Glu Gly Tyr Pro Cys Val Phe Tyr Gly Asp
             355                 360                 365
Tyr Tyr Gly Ile Pro Gln Tyr Asn Ile Pro Ser Leu Lys Ser Lys Ile
         370                 375                 380
Asp Pro Leu Leu Ile Ala Arg Arg Asp Tyr Ala Tyr Gly Thr Gln His
385                 390                 395                 400
Asp Tyr Leu Asp His Ser Asp Ile Ile Gly Trp Thr Arg Glu Gly Val
                 405                 410                 415
Thr Glu Lys Pro Gly Ser Gly Leu Ala Ala Leu Ile Thr Asp Gly Pro
             420                 425                 430
Gly Gly Ser Lys Trp Met Tyr Val Gly Lys Gln His Ala Gly Lys Val
         435                 440                 445
```

```
Phe Tyr Asp Leu Thr Gly Asn Arg Ser Asp Thr Val Thr Ile Asn Ser
            450                 455                 460

Asp Gly Trp Gly Glu Phe Lys Val Asn Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
                500                 505                 510

Ala Trp Pro
        515

<210> SEQ ID NO 17
<211> LENGTH: 412
<212> TYPE: PRT
<213> ORGANISM: Pyrococcus furiosus

<400> SEQUENCE: 17

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
                20                  25                  30

Ile Asp Thr Gly Ile Asp Ala Ser His Pro Asp Leu Gln Gly Lys Val
                35                  40                  45

Ile Gly Trp Val Asp Phe Val Asn Gly Arg Ser Tyr Pro Tyr Asp Asp
        50                  55                  60

His Gly His Gly Thr His Val Ala Ser Ile Ala Ala Gly Thr Gly Ala
65              70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
                100                 105                 110

Ile Lys Gly Val Glu Trp Ala Val Asp Asn Lys Asp Lys Tyr Gly Ile
                115                 120                 125

Lys Val Ile Asn Leu Ser Leu Gly Ser Ser Gln Ser Ser Asp Gly Thr
        130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                        165                 170                 175

Ser Pro Ala Ala Ala Ser Lys Val Ile Thr Val Gly Ala Val Asp Lys
                180                 185                 190

Tyr Asp Val Ile Thr Ser Phe Ser Ser Arg Gly Pro Thr Ala Asp Gly
                195                 200                 205

Arg Leu Lys Pro Glu Val Val Ala Pro Gly Asn Trp Ile Ile Ala Ala
        210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                        245                 250                 255

Ala Leu Leu Leu Gln Ala His Pro Ser Trp Thr Pro Asp Lys Val Lys
                260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
```

```
              290                 295                 300
Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
                340                 345                 350

Tyr Asp Pro Asn Gly Asn Gln Val Asp Tyr Ser Tyr Thr Ala Tyr Tyr
                355                 360                 365

Asp Phe Glu Lys Val Gly Tyr Tyr Asn Pro Thr Asp Gly Thr Trp Thr
                370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser
                405                 410

<210> SEQ ID NO 18
<211> LENGTH: 595
<212> TYPE: PRT
<213> ORGANISM: Pennicillium oxalicum

<400> SEQUENCE: 18

Arg Pro Asp Pro Lys Gly Gly Asn Leu Thr Pro Phe Ile His Lys Glu
1               5                   10                  15

Gly Glu Arg Ser Leu Gln Gly Ile Leu Asp Asn Leu Gly Gly Arg Gly
                20                  25                  30

Lys Lys Thr Pro Gly Thr Ala Ala Gly Leu Phe Ile Ala Ser Pro Asn
                35                  40                  45

Thr Glu Asn Pro Asn Tyr Tyr Tyr Thr Trp Thr Arg Asp Ser Ala Leu
50                  55                  60

Thr Ala Lys Cys Leu Ile Asp Leu Phe Glu Asp Ser Arg Ala Lys Phe
65                  70                  75                  80

Pro Ile Asp Arg Lys Tyr Leu Glu Thr Gly Ile Arg Asp Tyr Lys Ser
                85                  90                  95

Ser Gln Ala Ile Leu Gln Ser Val Ser Asn Pro Ser Gly Thr Leu Lys
                100                 105                 110

Asp Gly Ser Gly Leu Gly Glu Pro Lys Phe Glu Ile Asp Leu Asn Pro
                115                 120                 125

Phe Ser Gly Ala Trp Gly Arg Pro Gln Arg Asp Gly Pro Ala Leu Arg
                130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175

Ala Tyr Val Gly Gln Tyr Trp Asn Asn Thr Gly Phe Asp Leu Trp Glu
                180                 185                 190

Glu Val Asp Gly Ser Ser Phe Phe Thr Ile Ala Val Gln His Arg Ala
                195                 200                 205

Leu Val Glu Gly Ser Gln Leu Ala Lys Lys Leu Gly Lys Ser Cys Asp
                210                 215                 220

Ala Cys Asp Ser Gln Pro Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255
```

```
Ser Gly Ile Asp Leu Asp Ser Val Leu Gly Ser Ile His Thr Phe Asp
            260                 265                 270

Pro Glu Ala Ala Cys Asp Asp Ala Thr Phe Gln Pro Cys Ser Ala Arg
        275                 280                 285

Ala Leu Ala Asn His Lys Val Tyr Val Asp Ser Phe Arg Ser Ile Tyr
        290                 295                 300

Lys Ile Asn Ala Gly Leu Ala Glu Gly Ser Ala Ala Asn Val Gly Arg
305                 310                 315                 320

Tyr Pro Glu Asp Val Tyr Gln Gly Gly Asn Pro Trp Tyr Leu Ala Thr
                325                 330                 335

Leu Gly Ala Ser Glu Leu Leu Tyr Asp Ala Leu Tyr Gln Trp Asp Arg
        340                 345                 350

Leu Gly Lys Leu Glu Val Ser Glu Thr Ser Leu Ser Phe Phe Lys Asp
        355                 360                 365

Phe Asp Ala Thr Val Lys Ile Gly Ser Tyr Ser Arg Asn Ser Lys Thr
    370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
                405                 410                 415

Tyr Asp Arg Asn Thr Ala Ala Pro Leu Ser Ala Asn Asp Leu Thr Trp
            420                 425                 430

Ser Phe Ala Ser Phe Leu Thr Ala Thr Gln Arg Arg Asp Ala Val Val
        435                 440                 445

Pro Pro Ser Trp Gly Ala Lys Ser Ala Asn Lys Val Pro Thr Thr Cys
    450                 455                 460

Ser Ala Ser Pro Val Val Gly Thr Tyr Lys Ala Pro Thr Ala Thr Phe
465                 470                 475                 480

Ser Ser Lys Thr Lys Cys Val Pro Ala Lys Asp Ile Val Pro Ile Thr
                485                 490                 495

Phe Tyr Leu Ile Glu Asn Thr Tyr Tyr Gly Glu Asn Val Phe Met Ser
            500                 505                 510

Gly Asn Ile Thr Ala Leu Gly Asn Trp Asp Ala Lys Lys Gly Phe Pro
        515                 520                 525

Leu Thr Ala Asn Leu Tyr Thr Gln Asp Gln Asn Leu Trp Phe Ala Ser
    530                 535                 540

Val Glu Phe Ile Pro Ala Gly Thr Pro Phe Glu Tyr Lys Tyr Tyr Lys
545                 550                 555                 560

Val Glu Pro Asn Gly Asp Ile Thr Trp Glu Lys Gly Pro Asn Arg Val
                565                 570                 575

Phe Val Ala Pro Thr Gly Cys Pro Val Gln Pro His Ser Asn Asp Val
            580                 585                 590

Trp Gln Phe
        595

<210> SEQ ID NO 19
<211> LENGTH: 583
<212> TYPE: PRT
<213> ORGANISM: Artificial
<220> FEATURE:
<223> OTHER INFORMATION: Hybrid alpha-amylase

<400> SEQUENCE: 19

Ala Thr Ser Asp Asp Trp Lys Gly Lys Ala Ile Tyr Gln Leu Leu Thr
1               5                   10                  15
```

-continued

```
Asp Arg Phe Gly Arg Ala Asp Asp Ser Thr Ser Asn Cys Ser Asn Leu
            20                  25                  30
Ser Asn Tyr Cys Gly Gly Thr Tyr Glu Gly Ile Thr Lys His Leu Asp
        35                  40                  45
Tyr Ile Ser Gly Met Gly Phe Asp Ala Ile Trp Ile Ser Pro Ile Pro
    50                  55                  60
Lys Asn Ser Asp Gly Gly Tyr His Gly Tyr Trp Ala Thr Asp Phe Tyr
65                  70                  75                  80
Gln Leu Asn Ser Asn Phe Gly Asp Glu Ser Gln Leu Lys Ala Leu Ile
                85                  90                  95
Gln Ala Ala His Glu Arg Asp Met Tyr Val Met Leu Asp Val Val Ala
            100                 105                 110
Asn His Ala Gly Pro Thr Ser Asn Gly Tyr Ser Gly Tyr Thr Phe Asp
        115                 120                 125
Asp Ala Ser Leu Tyr His Pro Lys Cys Thr Ile Asp Tyr Asn Asn Gln
    130                 135                 140
Thr Ser Ile Glu Gln Cys Trp Val Ala Asp Glu Leu Pro Asp Ile Asp
145                 150                 155                 160
Thr Glu Asn Ser Asp Asn Val Ala Ile Leu Asn Asp Ile Val Ser Gly
                165                 170                 175
Trp Val Gly Asn Tyr Ser Phe Asp Gly Ile Arg Ile Asp Thr Val Lys
            180                 185                 190
His Ile Arg Lys Asp Phe Trp Thr Gly Tyr Ala Glu Ala Ala Gly Val
        195                 200                 205
Phe Ala Thr Gly Glu Val Phe Asn Gly Asp Pro Ala Tyr Val Gly Pro
    210                 215                 220
Tyr Gln Lys Tyr Leu Pro Ser Leu Ile Asn Tyr Pro Met Tyr Tyr Ala
225                 230                 235                 240
Leu Asn Asp Val Phe Val Ser Lys Ser Lys Gly Phe Ser Arg Ile Ser
                245                 250                 255
Glu Met Leu Gly Ser Asn Arg Asn Ala Phe Glu Asp Thr Ser Val Leu
            260                 265                 270
Thr Thr Phe Val Asp Asn His Asp Asn Pro Arg Phe Leu Asn Ser Gln
        275                 280                 285
Ser Asp Lys Ala Leu Phe Lys Asn Ala Leu Thr Tyr Val Leu Leu Gly
    290                 295                 300
Glu Gly Ile Pro Ile Val Tyr Tyr Gly Ser Glu Gln Gly Phe Ser Gly
305                 310                 315                 320
Gly Ala Asp Pro Ala Asn Arg Glu Val Leu Trp Thr Thr Asn Tyr Asp
            325                 330                 335
Thr Ser Ser Asp Leu Tyr Gln Phe Ile Lys Thr Val Asn Ser Val Arg
        340                 345                 350
Met Lys Ser Asn Lys Ala Val Tyr Met Asp Ile Tyr Val Gly Asp Asn
    355                 360                 365
Ala Tyr Ala Phe Lys His Gly Asp Ala Leu Val Val Leu Asn Asn Tyr
370                 375                 380
Gly Ser Gly Ser Thr Asn Gln Val Ser Phe Ser Val Ser Gly Lys Phe
385                 390                 395                 400
Asp Ser Gly Ala Ser Leu Met Asp Ile Val Ser Asn Ile Thr Thr Thr
                405                 410                 415
Val Ser Ser Asp Gly Thr Val Thr Phe Asn Leu Lys Asp Gly Leu Pro
            420                 425                 430
Ala Ile Phe Thr Ser Ala Thr Gly Gly Thr Thr Thr Thr Ala Thr Pro
```

```
                435                 440                 445
Thr Gly Ser Gly Ser Val Thr Ser Thr Ser Lys Thr Thr Ala Thr Ala
        450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Ala Thr Thr Tyr Gly Glu
                    485                 490                 495

Asn Ile Tyr Leu Val Gly Ser Ile Ser Gln Leu Gly Asp Trp Glu Thr
                500                 505                 510

Ser Asp Gly Ile Ala Leu Ser Ala Asp Lys Tyr Thr Ser Ser Asp Pro
            515                 520                 525

Leu Trp Tyr Val Thr Val Thr Leu Pro Ala Gly Glu Ser Phe Glu Tyr
        530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                    565                 570                 575

Thr Val Thr Asp Thr Trp Arg
                580

<210> SEQ ID NO 20
<211> LENGTH: 555
<212> TYPE: PRT
<213> ORGANISM: Gloeophyllum sepiarium

<400> SEQUENCE: 20

Ser Val Asp Ser Tyr Val Ser Ser Glu Gly Pro Ile Ala Lys Ala Gly
1               5                   10                  15

Val Leu Ala Asn Ile Gly Pro Asn Gly Ser Lys Ala Ser Gly Ala Ser
            20                  25                  30

Ala Gly Val Val Ala Ser Pro Ser Thr Ser Asp Pro Asp Tyr Trp
        35                  40                  45

Tyr Thr Trp Thr Arg Asp Ser Ser Leu Val Phe Lys Ser Leu Ile Asp
    50                  55                  60

Gln Tyr Thr Thr Gly Ile Asp Ser Thr Ser Ser Leu Arg Thr Leu Ile
65                  70                  75                  80

Asp Asp Phe Val Thr Ala Glu Ala Asn Leu Gln Gln Val Ser Asn Pro
                85                  90                  95

Ser Gly Thr Leu Thr Thr Gly Gly Leu Gly Glu Pro Lys Phe Asn Val
            100                 105                 110

Asp Glu Thr Ala Phe Thr Gly Ala Trp Gly Arg Pro Gln Arg Asp Gly
        115                 120                 125

Pro Ala Leu Arg Ser Thr Ala Leu Ile Thr Tyr Gly Asn Trp Leu Leu
    130                 135                 140

Ser Asn Gly Asn Thr Ser Tyr Val Thr Ser Asn Leu Trp Pro Ile Ile
145                 150                 155                 160

Gln Asn Asp Leu Gly Tyr Val Val Ser Tyr Trp Asn Gln Ser Thr Tyr
                165                 170                 175

Asp Leu Trp Glu Glu Val Asp Ser Ser Phe Phe Thr Thr Ala Val
            180                 185                 190

Gln His Arg Ala Leu Arg Glu Gly Ala Ala Phe Ala Thr Ala Ile Gly
        195                 200                 205

Gln Thr Ser Gln Val Ser Ser Tyr Thr Thr Gln Ala Asp Asn Leu Leu
    210                 215                 220
```

```
Cys Phe Leu Gln Ser Tyr Trp Asn Pro Ser Gly Tyr Ile Thr Ala
225                 230                 235                 240

Asn Thr Gly Gly Gly Arg Ser Gly Lys Asp Ala Asn Thr Leu Leu Ala
            245                 250                 255

Ser Ile His Thr Tyr Asp Pro Ser Ala Gly Cys Asp Ala Ala Thr Phe
            260                 265                 270

Gln Pro Cys Ser Asp Lys Ala Leu Ser Asn Leu Lys Val Tyr Val Asp
        275                 280                 285

Ser Phe Arg Ser Val Tyr Ser Ile Asn Ser Gly Val Ala Ser Asn Ala
        290                 295                 300

Ala Val Ala Thr Gly Arg Tyr Pro Glu Asp Ser Tyr Gln Gly Gly Asn
305                 310                 315                 320

Pro Trp Tyr Leu Thr Thr Phe Ala Val Ala Glu Gln Leu Tyr Asp Ala
                325                 330                 335

Leu Asn Val Trp Glu Ser Gln Gly Ser Leu Glu Val Thr Ser Thr Ser
                340                 345                 350

Leu Ala Phe Phe Gln Phe Ser Ser Val Thr Ala Gly Thr Tyr
        355                 360                 365

Ser Ser Ser Ser Ser Thr Tyr Ser Thr Leu Thr Ser Ala Ile Lys Asn
370                 375                 380

Phe Ala Asp Gly Phe Val Ala Ile Asn Ala Lys Tyr Thr Pro Ser Asn
385                 390                 395                 400

Gly Gly Leu Ala Glu Gln Tyr Ser Lys Ser Asp Gly Ser Pro Leu Ser
                405                 410                 415

Ala Val Asp Leu Thr Trp Ser Tyr Ala Ser Ala Leu Thr Ala Phe Glu
                420                 425                 430

Ala Arg Asn Asn Thr Gln Phe Ala Gly Trp Gly Ala Ala Gly Leu Thr
            435                 440                 445

Val Pro Ser Ser Cys Ser Gly Asn Ser Gly Gly Pro Thr Val Ala Val
            450                 455                 460

Thr Phe Asn Val Asn Ala Glu Thr Val Trp Gly Glu Asn Ile Tyr Leu
465                 470                 475                 480

Thr Gly Ser Val Asp Ala Leu Glu Asn Trp Ser Ala Asp Asn Ala Leu
                485                 490                 495

Leu Leu Ser Ser Ala Asn Tyr Pro Thr Trp Ser Ile Thr Val Asn Leu
            500                 505                 510

Pro Ala Ser Thr Ala Ile Glu Tyr Lys Tyr Ile Arg Lys Asn Asn Gly
            515                 520                 525

Ala Val Thr Trp Glu Ser Asp Pro Asn Asn Ser Ile Thr Thr Pro Ala
530                 535                 540

Ser Gly Ser Thr Thr Glu Asn Asp Thr Trp Arg
545                 550                 555

<210> SEQ ID NO 21
<211> LENGTH: 454
<212> TYPE: PRT
<213> ORGANISM: Artificial
<220> FEATURE:
<223> OTHER INFORMATION: Variant of a wt glucoamylase

<400> SEQUENCE: 21

Gln Ser Val Asp Ser Tyr Val Ser Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30
```

```
Ser Ala Gly Val Val Ala Ser Pro Ser Thr Ser Asp Pro Asp Tyr
         35                  40                  45
Trp Tyr Thr Trp Thr Arg Asp Ser Ser Leu Val Phe Lys Ser Leu Ile
 50                  55                  60
Asp Gln Tyr Thr Thr Gly Ile Asp Ser Thr Ser Ser Leu Arg Thr Leu
 65                  70                  75                  80
Ile Asp Asp Phe Val Thr Ala Glu Ala Asn Leu Gln Gln Val Pro Asn
                 85                  90                  95
Pro Ser Gly Thr Leu Thr Thr Gly Leu Gly Glu Pro Lys Phe Asn
                100                 105                 110
Val Asp Glu Thr Ala Phe Thr Gly Pro Trp Gly Arg Pro Gln Arg Asp
             115                 120                 125
Gly Pro Ala Leu Arg Ser Thr Ala Leu Ile Thr Tyr Gly Asn Trp Leu
             130                 135                 140
Leu Ser Asn Gly Asn Thr Ser Tyr Val Thr Ser Asn Leu Trp Pro Ile
145                 150                 155                 160
Ile Gln Asn Asp Leu Gly Tyr Val Val Ser Tyr Trp Asn Gln Ser Thr
                 165                 170                 175
Tyr Asp Leu Trp Glu Glu Val Asp Ser Ser Ser Phe Phe Thr Thr Ala
             180                 185                 190
Val Gln His Arg Ala Leu Arg Glu Gly Ala Ala Phe Ala Thr Ala Ile
             195                 200                 205
Gly Gln Thr Ser Gln Val Ser Ser Tyr Thr Thr Gln Ala Asp Asn Leu
             210                 215                 220
Leu Cys Phe Leu Gln Ser Tyr Trp Asn Pro Ser Gly Gly Tyr Ile Thr
225                 230                 235                 240
Ala Asn Thr Gly Gly Gly Arg Ser Gly Lys Asp Ala Asn Thr Leu Leu
                 245                 250                 255
Ala Ser Ile His Thr Tyr Asp Pro Ser Ala Gly Cys Asp Ala Ala Thr
             260                 265                 270
Phe Gln Pro Cys Ser Asp Lys Ala Leu Ser Asn Leu Lys Val Tyr Val
             275                 280                 285
Asp Ser Phe Arg Ser Val Trp Ser Ile Asn Ser Gly Val Ala Ser Asn
             290                 295                 300
Ala Ala Val Ala Thr Gly Arg Tyr Pro Glu Asp Ser Tyr Gln Gly Gly
305                 310                 315                 320
Asn Pro Trp Tyr Leu Thr Thr Phe Ala Val Ala Glu Gln Leu Tyr Asp
                 325                 330                 335
Ala Leu Asn Val Trp Glu Ser Gln Gly Ser Leu Glu Val Thr Ser Thr
             340                 345                 350
Ser Leu Ala Phe Phe Gln Gln Phe Ser Ser Gly Val Thr Ala Gly Thr
             355                 360                 365
Tyr Ser Ser Ser Ser Thr Tyr Ser Thr Leu Thr Ser Ala Ile Lys
             370                 375                 380
Asn Phe Ala Asp Gly Phe Val Ala Ile Asn Ala Lys Tyr Thr Pro Ser
385                 390                 395                 400
Asn Gly Gly Leu Ala Glu Gln Tyr Ser Lys Ser Asp Gly Ser Pro Leu
                 405                 410                 415
Ser Ala Val Asp Leu Thr Trp Ser Tyr Ala Ser Ala Leu Thr Ala Phe
             420                 425                 430
Glu Ala Arg Asn Asn Thr Gln Phe Ala Gly Trp Gly Ala Ala Gly Leu
             435                 440                 445
Thr Val Pro Ser Ser Cys
```

450

<210> SEQ ID NO 22
<211> LENGTH: 2201
<212> TYPE: DNA
<213> ORGANISM: Artificial
<220> FEATURE:
<223> OTHER INFORMATION: Hybrid alpha-amylase coding sequence

<400> SEQUENCE: 22

| | | | | | |
|---|---|---|---|---|---|
| atgaggtcct | tcagtgcttt | cctgcctttg | gcttctatga | tcactgctac | ctttgctcta | 60 |
| actcctgctc | aatggcgtgg | tcaatccata | tatcaagtcc | taactgaccg | ctttggacgt | 120 |
| actgatgatt | cgaccacagc | agcttgtgat | gttaatgact | attgtggtgg | atcatggcag | 180 |
| ggtatcatca | atcatcttga | ttatatccag | gatatgggat | tcagtgcggt | gagttaccag | 240 |
| attcggctat | cttgcatttg | caggcagagt | cggttgctga | gtatcttata | gatctggata | 300 |
| tctccagtgg | tggagaacct | ggttggggac | actcaagatg | gatccgccta | tcatggctac | 360 |
| tgggctcaga | acatatatgc | tctcaaccc | aattttggaa | cggtttcgga | tctcgtggcc | 420 |
| ctttctgctg | ctcttcatca | gcgcggaatg | gtaattctaa | aattctaaag | actaaatgga | 480 |
| gaattgctaa | ttagagacag | taccttatgg | tggatgtggt | gacaaaccat | atgggatatg | 540 |
| atggctgcgg | ggattgtgta | gactacagtg | tcttcacacc | gttcaactct | gtgagcctag | 600 |
| tttcatacga | tcttcgccat | ccaattgtct | cacactcaat | gggtagagac | taacgttttc | 660 |
| agcaatccta | tttccatccc | ttctgtctca | ttgactacaa | caattcgacc | agcatcaaag | 720 |
| tggtaagtaa | catccactct | gttctagtgc | catgctgaga | ttgtacagtg | ctgggaggga | 780 |
| gacaacattg | tatctcttcc | tgatatgaga | actgaagatt | cagacgtggc | aaccgagtgg | 840 |
| aatacctgga | tttcagaatt | ggtttcgaat | tacagcattg | acgggctacg | gattgacagt | 900 |
| gctcagcaag | tcgacaacgc | cttctttcca | ccgtttcaag | cagctgcggg | aggaattcat | 960 |
| gtccttggag | aagtcttcaa | tggtgatccg | aattatgtct | gccctatca | agactttatg | 1020 |
| agtggagttt | tgaactatcc | agcgtgagga | tctatatatc | attgcacaga | atactttcta | 1080 |
| atatcttcag | ttactactac | atcacccaag | ccttccaatc | taccagtggt | agcatcagca | 1140 |
| acctggttaa | tggcatcaac | caaatgaaga | gcacctgcac | agacaccacc | cttctcggat | 1200 |
| ccttcctcga | aaaccatgac | aaccccgct | tcccatccta | cacctcggat | ctctctctgg | 1260 |
| acaagaacgc | catcaccttc | accatcctcc | aagacggcat | cccatcatc | tacgaaggcc | 1320 |
| aagaacagca | ctactcgggt | ggcactgtcc | ctaacaaccg | agaagccatc | tggctctccg | 1380 |
| gctatgacaa | gtctgccccg | ctctacacct | ggattgcatc | cgtgaaccag | attagaaatc | 1440 |
| aggctatctt | taaggatagc | aactatctga | cctacatggc | ttggcctatc | tattcagacg | 1500 |
| catcgaccat | tgccatgcgg | aagggggttg | acggccttca | gatcatcagt | gtctactcaa | 1560 |
| ataaaggtgc | cagtgcagcc | agctatacca | tctcccttga | atcgagtact | actggcttca | 1620 |
| cggctaacga | ggcgctggtc | gaggtcatga | gttgtacgac | ctatactacg | gatgggagtg | 1680 |
| gtaacttagc | tgtgactatc | tctggcgggt | tgccggccgt | gttctatcct | aaggctcagt | 1740 |
| tggctgggag | tggaatatgt | ggggagactg | gcggcaccac | tacgacggct | accccactg | 1800 |
| gctccggcag | cgtgaccctc | gaccagcaaga | ccaccgcgac | tgccagcaag | accagcacca | 1860 |
| gtacgtcatc | aacctcctgt | accactccca | ccgccgtggc | tgtgactttc | gatctgacag | 1920 |
| ctaccaccac | ctacgcgag | aacatctacc | tggtcggatc | gatctctcag | ctgggtgact | 1980 |
| gggaaaccag | cgacggcata | gctctgagtg | ctgacaagta | cacttccagc | gacccgctct | 2040 |

```
ggtatgtcac tgtgactctg ccggctggtg agtcgtttga gtacaagttt atccgcattg   2100
agagcgatga ctccgtggag tgggagagtg atcccaaccg agaatacacc gttcctcagg   2160
cgtgcggaac gtcgaccgcg acggtgactg acacctggcg g                       2201
```

<210> SEQ ID NO 23
<211> LENGTH: 1920
<212> TYPE: DNA
<213> ORGANISM: Artificial
<220> FEATURE:
<223> OTHER INFORMATION: Hybrid alpha-amylase coding sequence

<400> SEQUENCE: 23

```
atgagattat cgacttcgag tctcttcctt tccgtgtctc tgctggggaa gctggccctc     60
gggctaactc ctgctcaatg cgtggtcaa tccatatatc aagtcctaac tgaccgcttt    120
ggacgtactg atgattcgac cacagcagct tgtgatgtta atgactattg tggtggatca    180
tggcagggta tcatcaatca tcttgattat atccaggata tgggattcag tgcgatctgg    240
atatctccag tggtggagaa cctggttggg gacactcaag atggatccgc ctatcatggc    300
tactgggctc agaacatata tgctctcaac cccaattttg gaacggtttc ggatctcgtg    360
gccctttctg ctgctcttca tcagcgcgga atgtacctta tggtggatgt ggtgacaaac    420
catatgggat atgatggctg cggggattgt gtagactaca gtgtcttcac accgttcaac    480
tctcaatcct atttccatcc cttctgtctc attgactaca caattcgac cagcatcaaa    540
gtgtgctggg agggagacaa cattgtatct cttcctgata tgagaactga agattcagac    600
gtggcaaccg agtggaatac ctggatttca gaattggttt cgaattacag cattgacggg    660
ctacggattg acagtgctca gcaagtcgac aacgccttct ttccaccgtt tcaagcagct    720
gcgggaggaa ttcatgtcct tggagaagtc ttcaatggta tccgaattac tgtctgcccc    780
tatcaagact ttatgagtgg agttttgaac tatccagctt actactacat cacccaagcc    840
ttccaatcta ccagtggtag catcagcaac ctggttaatg catcaaccaa atgaagagc    900
acctgcacag acaccaccct ctcggatcc ttcctcgaaa accatgacaa ccccccgcttc    960
ccatcctaca cctcggatct ctctctggac aagaacgcca tcaccttcac catcctccaa   1020
gacggcatcc ccatcatcta cgaaggccaa gaacagcact actcgggtgg cactgtccct   1080
aacaaccgag aagccatctg gctctccggc tatgacaagt ctgccccgct ctacacctgg   1140
attgcatccg tgaaccagat tagaaatcag gctatcttta aggatagcaa ctatctgacc   1200
tacatggctt ggcctatcta ttcagacgca tcgaccattg ccatgcggaa ggggtttgac   1260
ggccttcaga tcatcagtgt ctactcaaat aaaggtgcca gtgcagccag ctataccatc   1320
tcccttgaat cgagtactac tggcttcacg gctaacgagg cgctggtcga ggtcatgagt   1380
tgtacgacct atactacgga tgggagtggt aacttagctg tgactatctc tggcgggttg   1440
ccggccgtgt tctatcctaa ggctcagttg gctgggagtg aatatgttc aggcacaagc   1500
acaggttcct ggtcctcttc ttccgccact gccaccaaga ccagcacgtc ctccactgcc   1560
tccaaaaccg ccacaaccac caccacttcc tcaaccgctt gcacctctac ctccaccgtg   1620
gccgtgacgt tgaggtgac ggccacgacg gtctatggcc aggacatcaa ggtggtcggc   1680
tcgatcgcgg aactgggatc ctggagcccg tccagtgcga tcgcattaag cgcagaccgc   1740
tacacgagca gcaacccgct gtggtacggg acgtcaacg tgccggtgga caagacgttc   1800
gagtacaagt atattcgcgt gcagaatggc gcggtgactt gggagagcga tccgaatcgc   1860
```
agccttagcg tggcaggtgg ctgcggagta agtgggaaga cgcagaagga tacatggcgg    1920

<210> SEQ ID NO 24
<211> LENGTH: 1923
<212> TYPE: DNA
<213> ORGANISM: Artificial
<220> FEATURE:
<223> OTHER INFORMATION: Hybrid alpha-amylase coding sequence

<400> SEQUENCE: 24

| | |
|---|---:|
| atgagattat cgacttcgag tctcttcctt tccgtgtctc tgctggggaa gctggccctc | 60 |
| gggctaactc ctgctcaatg gcgtggtcaa tccatatatc aagtcctaac tgaccgcttt | 120 |
| ggacgtactg atgattcgac cacagcagct tgtgatgtta atgactattg tggtggatca | 180 |
| tggcagggta tcatcaatca tcttgattat atccaggata tgggattcag tcgatctgg | 240 |
| atatctccag tggtggagaa cctggttggg gacactcaag atggatccgc ctatcatggc | 300 |
| tactgggctc agaacatata tgctctcaac cccaattttg gaacggtttc ggatctcgtg | 360 |
| gccctttctg ctgctcttca tcagcgcgga atgtaccta tggtggatgt ggtgacaaac | 420 |
| catatgggat atgatggctg cggggattgt gtagactaca gtgtcttcac accgttcaac | 480 |
| tctcaatcct atttccatcc cttctgtctc attgactaca caattcgac cagcatcaaa | 540 |
| gtgtgctggg agggagacaa cattgtatct cttcctgata tgagaactga agattcagac | 600 |
| gtggcaaccg agtggaatac ctggatttca gaattggttt cgaattacag cattgacggg | 660 |
| ctacggattg acagtgctca gcaagtcgac aacgccttct ttccaccgtt tcaagcagct | 720 |
| gcgggaggaa ttcatgtcct tggagaagtc ttcaatggtg atccgaatta tgtctgcccc | 780 |
| tatcaagact ttatgagtgg agttttgaac tatccagctt actactacat caccccaagcc | 840 |
| ttccaatcta ccagtggtag catcagcaac ctggttaatg gcatcaacca aatgaagagc | 900 |
| acctgcacag acaccaccct tctcggatcc ttcctcgaaa ccatgacaa ccccccgcttc | 960 |
| ccatcctaca cctcggatct ctctctggac aagaacgcca tcaccttcac catcctccaa | 1020 |
| gacggcatcc ccatcatcta cgaaggccaa gaacagcact actcgggtgg cactgtccct | 1080 |
| aacaaccgag aagccatctg gctctccggc tatgacaagt ctgccccgct ctacacctgg | 1140 |
| attgcatccg tgaaccagat tagaaatcag gctatcttta aggatagcaa ctatctgacc | 1200 |
| tacatggctt ggcctatcta ttcagacgca tcgaccattg ccatgcggaa ggggtttgac | 1260 |
| ggccttcaga tcatcagtgt ctactcaaat aaaggtgcca gtgcagccag ctataccatc | 1320 |
| tcccttgaat cgagtactac tggcttcacg gctaacgagg cgctggtcga ggtcatgagt | 1380 |
| tgtacgacct atactacgga tgggagtggt aacttagctg tgactatctc tggcgggttg | 1440 |
| ccggccgtgt tctatcctaa ggctcagttg gctgggagtg aatatgtac tggcggcacc | 1500 |
| actacgacgc ctaccccac tggctccggc agcgtgacct cgaccagcaa gaccaccgcg | 1560 |
| actgccagca agaccagcac cagtacgtca tcaacctcct gtaccactcc caccgccgtg | 1620 |
| gccgtcacat ttaatgtgat tgcaactact gcctatggtg agaacgtcaa gcttgcagga | 1680 |
| tccatttctc agcttggaag ctggagtacg agcagtgcta ttgcactgag cgcttcgagc | 1740 |
| tacaccagta gcaatcacct ttggtttgtt actgcgactc tgcccgctgg aacaaccttc | 1800 |
| tcatacaagt acattcgtgt taagagcgat ggcagtattc agtgggagag tgaccccaac | 1860 |
| cggtcctaca cagtgccagc agtctgtggt actacatcgg tcactattag tgacacctgg | 1920 |
| agg | 1923 |

POLYPEPTIDES HAVING ALPHA-AMYLASE ACTIVITY AND POLYNUCLEOTIDES ENCODING SAME

CROSS-REFERENCE TO RELATED APPLICATIONS

This application is a 35 U.S.C. 371 national application of international application no. PCT/EP2019/058771 filed Apr. 8, 2019, which claims priority or the benefit under 35 U.S.C. 119 of European application no. 18166236.2 filed Apr. 9, 2018, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having alpha-amylase activity, catalytic domains, and polynucleotides encoding the polypeptides, catalytic domains. The invention also relates to nucleic acid constructs, vectors, and host cells comprising the polynucleotides as well as methods of producing and using the polypeptides, and catalytic domains.

Description of the Related Art

Alpha-amylases (1,4-α-D-glucan glucanohydrolase, EC 3.2.1.1) constitute a group of enzymes which catalyze hydrolysis of starch and other linear and branched 1,4-glucosidic oligo- and polysaccharides.

Another group of alpha-amylases are referred to as "Fungamyl™-like alpha-amylases", which are alpha-amylases related or homologous to the alpha-amylase derived from *Aspergillus oryzae*. The Fungamyl-like alpha-amylases have a relatively low thermostability e.g. the commercial product sold under the tradename FUNGAMYL™ by Novozymes A/S, Denmark, has an optimum around 55° C., and is not suitable for processes carried out at high temperatures. Fungamyl™-like alpha-amylases are today used for making syrups for, e.g., the brewing industry.

An alpha-amylase with increased thermo-stability, preferably at an acidic pH, has previously been successfully isolated. WO2004/055178 discloses a gene from *Rhizomucor pusillus* encoding an alpha-amylase denoted AM782. Characterization of this amylase has shown it to be a highly thermo-acidophilic alpha-amylase. The amylase AM782 can work at a very high temperature, at least up to 70° C. CBM-containing hybrid enzymes, as well as detailed descriptions of the preparation and purification thereof, are known in the art (see, e.g., WO 90/00609, WO 94/24158 and WO 95/16782, WO 2006/069290, as well as Greenwood et al. *Biotechnology and Bioengineering* 44 (1994) pp. 1295-1305). WO2006/069290 discloses hybrid alpha-amylases comprising the catalytic core (AM782) combined with a linker and a starch binding domain derived from a glucolamylase from *Aspergillus niger*. This hybrid has been used for over a decade as a commercial product used in saccharification of starch-containing material.

WO2013/006756 discloses variants of the AM782 alpha-amylase having improved thermo-stability over the parent alpha-amylase.

There is still a need for identifying fungal acid alpha-amylases suitable for use in commercial processes, e.g., in a saccharification step in an ethanol production process from starch-containing material.

SUMMARY OF THE INVENTION

The present invention provides hybrid polypeptides having alpha-amylase activity, selected from a first polypeptide sequence comprising a catalytic core, and a second polypeptide sequence comprising a carbohydrate binding module (CBM), wherein
(a) the catalytic core is selected from a polypeptide having at least 80%, at least 85%, at least 90%, at least 91%, at least 92%, at least 93%, at least 94%, at least 95%, at least 96%, at least 97%, at least 98%, at least 99% or 100% sequence identity to amino acids 20 to 494 of SEQ ID NO: 1 or amino acids 20 to 496 of SEQ ID NO: 1; and
(b) the CBM is selected from a polypeptide having at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 4, SEQ ID NO: 5, and SEQ ID NO: 6.

The present invention also relates to polynucleotides encoding the polypeptides of the present invention; nucleic acid constructs; recombinant expression vectors; recombinant host cells comprising the polynucleotides; and methods of producing the polypeptides.

The present invention also relates to polypeptides comprising a catalytic domain selected from the group consisting of:
(a) a catalytic domain having at least 80%, at least 85%, at least 90%, at least 91%, at least 92%, at least 93%, at least 94%, at least 95%, at least 96%, at least 97%, at least 98%, at least 99% or 100% sequence identity to amino acids 20 to 494 of SEQ ID NO: 1 or amino acids 20 to 496 of SEQ ID NO: 1;
(b) a catalytic domain encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to nucleotides 58 to 1766 of SEQ ID NO: 10, or the cDNA sequence thereof;
(c) a fragment of the catalytic domain of (a), or (b) that has alpha-amylase activity.

The present invention also relates to a process of producing a fermentation product from starch-containing material comprising the steps of: (a) liquefying starch-containing material above the initial gelatinization temperature of said starch-containing material in the presence of an alpha amylase; (b) saccharifying the liquefied material; and (c) fermenting with a fermenting organism; wherein step (b) is carried out using at least an alpha-amylase of the invention, and optionally a glucoamylase.

The present invention also relates to a process of producing a fermentation product from raw starch material, comprising the steps of: (a) saccharifying starch-containing material at a temperature below the initial gelatinization temperature of said starch-containing material; and (b) fermenting with a fermenting organism, wherein step (a) is carried out using at least an alpha-amylase of the invention, and optionally a glucoamylase.

The present invention also relates to a process of producing a syrup product from starch-containing material, comprising the step of: (a) liquefying starch-containing material at a temperature above the initial gelatination temperature of said starch-containing material in the presence of an alpha amylase; (b) saccharifying the liquefied material in the presence of an alpha-amylase of the invention, and optionally a glucoamylase.

Definitions

Alpha-amylase: Alpha-amylases (E. C. 3.2.1.1) are a group of enzymes which catalyze the hydrolysis of starch and other linear and branched 1,4 glucosidic oligo- and polysaccharides. The skilled person will know how to determine alpha-amylase activity. It may be determined according to the procedure described in the Examples, e.g., by measuring residual activity at pH 4.0 using a commercial alpha-amylase colorimetric assay kit (Kikkoman Biochemifa Company) or by measuring raw starch activity. In one aspect, the polypeptides of the present invention have at least 20%, e.g., at least 40%, at least 50%, at least 60%, at least 70%, at least 80%, at least 90%, at least 95%, or at least 100% of the alpha-amylase activity (residual or raw starch) of the polypeptide of SEQ ID NO: 1. In one aspect, the polypeptides of the present invention have at least 20%, e.g., at least 40%, at least 50%, at least 60%, at least 70%, at least 80%, at least 90%, at least 95%, or at least 100% of the alpha-amylase activity (residual or raw starch) of the polypeptide of SEQ ID NO: 7. In one aspect, the polypeptides of the present invention have at least 20%, e.g., at least 40%, at least 50%, at least 60%, at least 70%, at least 80%, at least 90%, at least 95%, or at least 100% of the alpha-amylase activity (residual or raw starch) of the polypeptide of SEQ ID NO: 8. In one aspect, the polypeptides of the present invention have at least 20%, e.g., at least 40%, at least 50%, at least 60%, at least 70%, at least 80%, at least 90%, at least 95%, or at least 100% of the alpha-amylase activity (residual or raw starch) of the polypeptide of SEQ ID NO: 9.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Carbohydrate Binding Module: The term "carbohydrate binding module" means a polypeptide amino acid sequence which binds preferentially to a poly- or oligosaccharide (carbohydrate), frequently—but not necessarily exclusively—to a water-insoluble (including crystalline) form thereof. A carbohydrate-binding module (CBM), is often referred to, a carbohydrate-binding domain (CBD).

CBMs derived from starch degrading enzymes are often referred to as starch-binding modules or SBMs (which may occur in certain amylolytic enzymes, such as certain glucoamylases (GA), or in enzymes such as cyclodextrin glucanotransferases, or in alpha-amylases). SBMs are often referred to as SBDs (Starch Binding Domains).

The "Carbohydrate-Binding Module of Family 20" or a CBM-20 module is in the context of this invention defined as a sequence of approximately 100 amino acids having at least 45% homology to the Carbohydrate-Binding Module (CBM) of the polypeptide disclosed in FIG. 1 by Joergensen et al. (1997) in Biotechnol. Lett. 19:1027-1031. The CBM comprises the last 102 amino acids of the polypeptide, i.e., the subsequence from amino acid 582 to amino acid 683. The numbering of Glycoside Hydrolase Families applied in this disclosure follows the concept of Coutinho, P. M. & Henrissat, B. (1999) *CAZy—Carbohydrate Active Enzymes server* at URL: http://afmb.cnrs-mrs.fr/~cazy/CAZY/index-.html or alternatively Coutinho, P. M. & Henrissat, B. 1999; The modular structure of cellulases and other carbohydrate-active enzymes: an integrated database approach. In "*Genetics, Biochemistry and Ecology of Cellulose Degradation*", K. Ohmiya, K. Hayashi, K. Sakka, Y. Kobayashi, S. Karita and T. Kimura eds., Uni Publishers Co., Tokyo, pp. 15-23 and Bourne, Y. & Henrissat, B. 2001; Glycoside hydrolases and glycosyltransferases: families and functional modules, *Current Opinion in Structural Biology* 11:593-600.

Examples of enzymes which comprise a CBM suitable for use in the context of the invention are alpha-amylases, maltogenic alpha-amylases, cellulases, xylanases, mannanases, arabinofuranosidases, acetylesterases and chitinases. Further CBMs of interest in relation to the present invention include CBMs deriving from glucoamylases (EC 3.2.1.3) or from CGTases (EC 2.4.1.19).

Preferred are hybrids comprising a CBM of Carbohydrate-Binding Module Family 20, 21 or 25.

Catalytic domain: The term "catalytic domain" means the region of an enzyme containing the catalytic machinery of the enzyme. In one embodiment the catalytic domain comprises or consists of amino acids 20-494 of SEQ ID NO: 1, or amino acids 20-496 of SEQ ID NO: 1.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression. In one embodiment, the control sequence(s) is heterologous to the polynucleotide of the present invention.

Fragment: The term "fragment" means a polypeptide or a catalytic domain having one or more (e.g., several) amino acids absent from the amino and/or carboxyl terminus of a mature polypeptide or domain; wherein the fragment has alpha-amylase activity. In one aspect, a fragment contains at least 475 amino acid residues (e.g., amino acids 20 to 494 of SEQ ID NO: 1).

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Hybrid polypeptide or hybrid enzyme: The terms "hybrid enzyme" or "hybrid polypeptide" is used herein to characterize those of the polypeptides of the invention that comprises a first amino acid sequence comprising at least one catalytic module having alpha-amylase activity and a second amino acid sequence comprising at least one carbohydrate-binding module wherein the first and the second sequences are derived from different sources. The term "source" being understood as, e.g., but not limited to a parent enzyme, e.g., an amylase or glucoamylase, or other catalytic activity comprising a suitable catalytic module and/or a suitable CBM and/or a suitable linker.

Initial gelatinization temperature: The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, Starch/Stärke 44(12): 461-466.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 20 to 496 of SEQ ID NO: 1. In another aspect the mature polypeptide is amino acids 20 to 494 of SEQ ID NO: 1. Amino acids 1 to 19 of SEQ ID NO: 1 are a signal peptide. It is known in the art that a host cell may produce a mixture of two or more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having alpha-amylase activity. In one aspect, the mature polypeptide coding sequence is nucleotides 58 to 1766 of SEQ ID NO: 10 or the cDNA sequence thereof, and nucleotides 1 to 57 of SEQ ID NO: 10 encode a signal peptide. In another embodiment, the mature polypeptide coding sequence (without introns) is nucleotides 58 to 228, 292 to 450, 501 to 590, 663 to 722, 769 to 1043, 1091 to 1766 of SEQ ID NO: 10.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences. In one embodiment, the one or more control sequences are heterologous to the polynucleotide of the present invention.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having alpha-amylase activity.

Variant: The term "variant" means a polypeptide having alpha-amylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

DETAILED DESCRIPTION OF THE INVENTION

Polypeptides Having Alpha-Amylase Activity

In one aspect, the present invention relates to hybrid alpha-amylases comprising the catalytic core derived from an alpha-amylase from *Acidomyces acidothermus* and at least a carbohydrate binding module.

In one embodiment, the present invention relates to a hybrid polypeptide having alpha-amylase activity, selected from a first polypeptide sequence comprising a catalytic core, and a second polypeptide sequence comprising a carbohydrate binding module (CBM), wherein (a) the catalytic core is selected from a polypeptide having at least 80%, at least 85%, at least 90%, at least 91%, at least 92%, at least 93%, at least 94%, at least 95%, at least 96%, at least 97%, at least 98%, at least 99% or 100% sequence identity to amino acids 20 to 494 of SEQ ID NO: 1 or amino acids 20 to 496 of SEQ ID NO: 1; and (b) the CBM is selected from a polypeptide having at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 4, SEQ ID NO: 5, or SEQ ID NO: 6.

In one embodiment, the hybrid alpha-amylase may comprise a linker. The linker may comprise a sequence from about 2 to about 100 amino acid residues, more preferably from 10 to 50 amino acid residues, such as from 15 to 25 amino acid residues. More particularly the linker may in one embodiment be selected from a polypeptide having at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 2 or SEQ ID NO: 3.

In one embodiment, the hybrid alpha-amylase is selected from a polypeptide having 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 7, SEQ ID NO: 8, or SEQ ID NO: 9.

In an embodiment, the present invention relates to a hybrid polypeptide having a sequence identity to the polypeptide of SEQ ID NO: 7 of at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In one aspect, the polypeptides differ by up to 10 amino acids, e.g., 1, 2, 3, 4, 5, 6, 7, 8, 9, or 10, from the polypeptide of SEQ ID NO: 7.

In a particular embodiment the invention relates to polypeptides having a sequence identity to the polypeptide of SEQ ID NO: 7 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the alpha-amylase activity of the polypeptide of SEQ ID NO: 7.

In a particular embodiment the invention relates to polypeptides having a sequence identity to the polypeptide of SEQ ID NO: 7 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the alpha-amylase activity of the polypeptide of SEQ ID NO: 7.

In a particular embodiment the invention relates to polypeptides having a sequence identity to the polypeptide of SEQ ID NO: 7 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the alpha-amylase activity of the polypeptide of SEQ ID NO: 7.

In a particular embodiment the invention relates to polypeptides having a sequence identity to the polypeptide of SEQ ID NO: 7 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the alpha-amylase activity of the polypeptide of SEQ ID NO: 7.

In a particular embodiment the invention relates to polypeptides having a sequence identity to the polypeptide of SEQ ID NO: 7 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the alpha-amylase activity of the polypeptide of SEQ ID NO: 7.

In a particular embodiment the invention relates to polypeptides having a sequence identity to the polypeptide of SEQ ID NO: 7 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the alpha-amylase activity of the polypeptide of SEQ ID NO: 7.

In a particular embodiment the invention relates to polypeptides having a sequence identity to the polypeptide of SEQ ID NO: 7 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the alpha-amylase activity of the polypeptide of SEQ ID NO: 7.

In an embodiment, the present invention relates to a hybrid polypeptide having a sequence identity to the polypeptide of SEQ ID NO: 8 of at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In one aspect, the polypeptides differ by up to 10 amino acids, e.g., 1, 2, 3, 4, 5, 6, 7, 8, 9, or 10, from the polypeptide of SEQ ID NO: 8.

In a particular embodiment the invention relates to polypeptides having a sequence identity to the polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the alpha-amylase activity of the polypeptide of SEQ ID NO: 8.

In a particular embodiment the invention relates to polypeptides having a sequence identity to the polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the alpha-amylase activity of the polypeptide of SEQ ID NO: 8.

In a particular embodiment the invention relates to polypeptides having a sequence identity to the polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the alpha-amylase activity of the polypeptide of SEQ ID NO: 8.

In a particular embodiment the invention relates to polypeptides having a sequence identity to the polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the alpha-amylase activity of the polypeptide of SEQ ID NO: 8.

In a particular embodiment the invention relates to polypeptides having a sequence identity to the polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the alpha-amylase activity of the polypeptide of SEQ ID NO: 8.

In a particular embodiment the invention relates to polypeptides having a sequence identity to the polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the alpha-amylase activity of the polypeptide of SEQ ID NO: 8.

In a particular embodiment the invention relates to polypeptides having a sequence identity to the polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the alpha-amylase activity of the polypeptide of SEQ ID NO: 8.

In an embodiment, the present invention relates to a hybrid polypeptide having a sequence identity to the polypeptide of SEQ ID NO: 9 of at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have alpha-amylase activity. In one aspect, the polypeptides differ by up to 10 amino acids, e.g., 1, 2, 3, 4, 5, 6, 7, 8, 9, or 10, from the polypeptide of SEQ ID NO: 9.

In a particular embodiment the invention relates to polypeptides having a sequence identity to the polypeptide of SEQ ID NO: 9 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the alpha-amylase activity of the polypeptide of SEQ ID NO: 9.

In a particular embodiment the invention relates to polypeptides having a sequence identity to the polypeptide of SEQ ID NO: 9 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the alpha-amylase activity of the polypeptide of SEQ ID NO: 9.

In a particular embodiment the invention relates to polypeptides having a sequence identity to the polypeptide of SEQ ID NO: 9 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the alpha-amylase activity of the polypeptide of SEQ ID NO: 9.

In a particular embodiment the invention relates to polypeptides having a sequence identity to the polypeptide of SEQ ID NO: 9 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the alpha-amylase activity of the polypeptide of SEQ ID NO: 9.

In a particular embodiment the invention relates to polypeptides having a sequence identity to the polypeptide of SEQ ID NO: 9 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the alpha-amylase activity of the polypeptide of SEQ ID NO: 9.

In a particular embodiment the invention relates to polypeptides having a sequence identity to the polypeptide of SEQ ID NO: 9 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the alpha-amylase activity of the polypeptide of SEQ ID NO: 9.

In a particular embodiment the invention relates to polypeptides having a sequence identity to the polypeptide of SEQ ID NO: 9 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the alpha-amylase activity of the polypeptide of SEQ ID NO: 9.

In an embodiment, the polypeptide has been isolated. A polypeptide of the present invention preferably comprises or consists of the amino acid sequence of SEQ ID NO: 7, SEQ ID NO: 8, or SEQ ID NO: 9 or an allelic variant thereof; or is a fragment thereof having alpha-amylase activity.

In another embodiment, the present invention relates to a polypeptide having alpha-amylase activity encoded by a polynucleotide having a sequence identity to the mature polypeptide coding sequence of SEQ ID NO: 10 or the cDNA sequence thereof of at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having alpha-amylase activity encoded by a polynucleotide having a sequence identity to nucleotides 58 to 228, 292 to 450, 501 to 590, 663 to 722, 769 to 1043, 1091 to 1766 of SEQ ID NO: 10 of at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having alpha-amylase activity encoded by a polynucleotide having a sequence identity to the mature polypeptide coding sequence of SEQ ID NO: 22 or the cDNA sequence thereof of at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having alpha-amylase activity encoded by a polynucleotide having a sequence identity to nucleotides 58 to 228, 292 to 450, 501 to 590, 663 to 722, 769 to 1043, 1091 to 2201 of SEQ ID NO: 22 of at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having alpha-amylase activity encoded by a polynucleotide having a sequence identity to nucleotides 64 to 1920 of SEQ ID NO: 23 of at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having alpha-amylase activity encoded by a polynucleotide having a sequence identity to nucleotides 64 to 1923 of SEQ ID NO: 24 of at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptides of SEQ ID NO: 1, SEQ ID NO: 7, SEQ ID NO: 8, or SEQ ID NO: 9 comprising a substitution, deletion, and/or insertion at one or more (e.g., several) positions. In an embodiment, the number of amino acid substitutions, deletions and/or insertions introduced into the mature polypeptide of SEQ ID NO: 1, SEQ ID NO: 7, SEQ ID NO: 8, or SEQ ID NO: 9 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The terms "hybrid enzyme" or "hybrid polypeptide" is used herein to characterize those of the polypeptides of the invention that comprises a first amino acid sequence comprising at least one catalytic module having alpha-amylase activity and a second amino acid sequence comprising at least one carbohydrate-binding module wherein the first and the second are derived from different sources. The term "source" being understood as, e.g., but not limited to a parent enzyme, e.g., an amylase or glucoamylase, or other catalytic activity comprising a suitable catalytic module and/or a suitable CBM and/or a suitable linker.

The Enzyme classification numbers (EC numbers) are in accordance with the *Recommendations* (1992) *of the Nomenclature Committee of the International Union of Biochemistry and Molecular Biology*, Academic Press Inc, 1992.

Polypeptides as referred to herein include species comprising an amino acid sequence of an alpha-amylase enzyme (EC 3.2.1.1) linked (i.e., covalently bound) to an amino acid sequence comprising a carbohydrate-binding module (CBM).

CBM-containing hybrid enzymes, as well as detailed descriptions of the preparation and purification thereof, are known in the art (see, e.g., WO 90/00609, WO 94/24158 and WO 95/16782, WO 2006/069290, as well as Greenwood et al. *Biotechnology and Bioengineering* 44 (1994) pp. 1295-1305). They may, e.g., be prepared by transforming into a host cell a DNA construct comprising at least a fragment of DNA encoding the carbohydrate-binding module ligated, with or without a linker, to a DNA sequence encoding the polypeptide of interest, and growing the transformed host cell to express the fused gene. The CBM in a polypeptide of the invention may be positioned C-terminally, N-terminally or internally in polypeptide. In an embodiment a polypeptide may comprise more than one CBM, e.g., two CBMs; one positioned C-terminally, the other N-terminally or the two CBMs in tandem positioned C-terminally, N-terminally or internally.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

Catalytic Domains

In one embodiment, the present invention also relates to catalytic domains having a sequence identity to amino acids 20 to 494 of SEQ ID NO: 1 of at least 80%, at least 85%, at least 90%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 20 to 494 of SEQ ID NO: 1.

The catalytic domain preferably comprises or consists of amino acids 20 to 494 of SEQ ID NO: 1 or an allelic variant thereof; or is a fragment thereof having alpha-amylase activity.

In one embodiment, the present invention also relates to catalytic domains having a sequence identity to amino acids 20 to 496 of SEQ ID NO: 1 of at least 80%, at least 85%, at least 90%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 20 to 496 of SEQ ID NO: 1.

The catalytic domain preferably comprises or consists of amino acids 20 to 496 of SEQ ID NO: 1 or an allelic variant thereof; or is a fragment thereof having alpha-amylase activity.

In one embodiment, the present invention also relates to a catalytic domain having a sequence identity to amino acids 20 to 494 of SEQ ID NO: 1 of at least 80%, at least 85%, at least 90%, at least 95%, at least 96%, at least 97%, at least 98%, at least 99%, or 100%, and wherein the catalytic domain has at least at least 70% of the alpha-amylase activity of amino acids 20 to 494 of SEQ ID NO: 1.

In one embodiment, the present invention also relates to a catalytic domain having a sequence identity to amino acids 20 to 494 of SEQ ID NO: 1 of at least 80%, at least 85%, at least 90%, at least 95%, at least 96%, at least 97%, at least 98%, at least 99%, or 100%, and wherein the catalytic domain has at least at least 75% of the alpha-amylase activity of amino acids 20 to 494 of SEQ ID NO: 1.

In one embodiment, the present invention also relates to a catalytic domain having a sequence identity to amino acids 20 to 494 of SEQ ID NO: 1 of at least 80%, at least 85%, at least 90%, at least 95%, at least 96%, at least 97%, at least 98%, at least 99%, or 100%, and wherein the catalytic domain has at least at least 80% of the alpha-amylase activity of amino acids 20 to 494 of SEQ ID NO: 1.

In one embodiment, the present invention also relates to a catalytic domain having a sequence identity to amino acids 20 to 494 of SEQ ID NO: 1 of at least 80%, at least 85%, at least 90%, at least 95%, at least 96%, at least 97%, at least 98%, at least 99%, or 100%, and wherein the catalytic domain has at least at least 85% of the alpha-amylase activity of amino acids 20 to 494 of SEQ ID NO: 1.

In one embodiment, the present invention also relates to a catalytic domain having a sequence identity to amino acids 20 to 494 of SEQ ID NO: 1 of at least 80%, at least 85%, at least 90%, at least 95%, at least 96%, at least 97%, at least 98%, at least 99%, or 100%, and wherein the catalytic domain has at least at least 90% of the alpha-amylase activity of amino acids 20 to 494 of SEQ ID NO: 1.

In one embodiment, the present invention also relates to a catalytic domain having a sequence identity to amino acids 20 to 494 of SEQ ID NO: 1 of at least 80%, at least 85%, at least 90%, at least 95%, at least 96%, at least 97%, at least 98%, at least 99%, or 100%, and wherein the catalytic domain has at least at least 95% of the alpha-amylase activity of amino acids 20 to 494 of SEQ ID NO: 1.

In one embodiment, the present invention also relates to a catalytic domain having a sequence identity to amino acids 20 to 494 of SEQ ID NO: 1 of at least 80%, at least 85%, at least 90%, at least 95%, at least 96%, at least 97%, at least 98%, at least 99%, or 100%, and wherein the catalytic domain has at least at least 100% of the alpha-amylase activity of amino acids 20 to 494 of SEQ ID NO: 1. In one embodiment, the present invention also relates to a catalytic domain having a sequence identity to amino acids 20 to 496 of SEQ ID NO: 1 of at least 80%, at least 85%, at least 90%, at least 95%, at least 96%, at least 97%, at least 98%, at least 99%, or 100%, and wherein the catalytic domain has at least at least 70% of the alpha-amylase activity of amino acids 20 to 496 of SEQ ID NO: 1.

In one embodiment, the present invention also relates to a catalytic domain having a sequence identity to amino acids 20 to 496 of SEQ ID NO: 1 of at least 80%, at least 85%, at least 90%, at least 95%, at least 96%, at least 97%, at least 98%, at least 99%, or 100%, and wherein the catalytic domain has at least at least 75% of the alpha-amylase activity of amino acids 20 to 496 of SEQ ID NO: 1.

In one embodiment, the present invention also relates to a catalytic domain having a sequence identity to amino acids 20 to 496 of SEQ ID NO: 1 of at least 80%, at least 85%, at least 90%, at least 95%, at least 96%, at least 97%, at least 98%, at least 99%, or 100%, and wherein the catalytic domain has at least at least 80% of the alpha-amylase activity of amino acids 20 to 496 of SEQ ID NO: 1.

In one embodiment, the present invention also relates to a catalytic domain having a sequence identity to amino acids 20 to 496 of SEQ ID NO: 1 of at least 80%, at least 85%, at least 90%, at least 95%, at least 96%, at least 97%, at least 98%, at least 99%, or 100%, and wherein the catalytic domain has at least at least 85% of the alpha-amylase activity of amino acids 20 to 496 of SEQ ID NO: 1.

In one embodiment, the present invention also relates to a catalytic domain having a sequence identity to amino acids 20 to 496 of SEQ ID NO: 1 of at least 80%, at least 85%, at least 90%, at least 95%, at least 96%, at least 97%, at least 98%, at least 99%, or 100%, and wherein the catalytic domain has at least at least 90% of the alpha-amylase activity of amino acids 20 to 496 of SEQ ID NO: 1.

In one embodiment, the present invention also relates to a catalytic domain having a sequence identity to amino acids 20 to 496 of SEQ ID NO: 1 of at least 80%, at least 85%, at least 90%, at least 95%, at least 96%, at least 97%, at least 98%, at least 99%, or 100%, and wherein the catalytic domain has at least at least 95% of the alpha-amylase activity of amino acids 20 to 496 of SEQ ID NO: 1.

In one embodiment, the present invention also relates to a catalytic domain having a sequence identity to amino acids 20 to 496 of SEQ ID NO: 1 of at least 80%, at least 85%, at least 90%, at least 95%, at least 96%, at least 97%, at least 98%, at least 99%, or 100%, and wherein the catalytic domain has at least at least 100% of the alpha-amylase activity of amino acids 20 to 496 of SEQ ID NO: 1.

In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) the nucleotides 58 to 1766 of SEQ ID NO: 10, (ii) or the cDNA sequence thereof, or (iii) the full-length complement of (i) or (ii) (Sambrook et al., 1989, supra).

In another embodiment, the present invention also relates to catalytic domains encoded by polynucleotides having a sequence identity to nucleotides 58 to 1766 of SEQ ID NO: 10 or the cDNA sequence thereof of at least 60%, e.g., at least 65%, at least 70%, at least 75%, at least 80%, at least 85%, at least 90%, at least 95%, at least 96%, at least 97%, at least 98%, at least 99%, or 100%.

The polynucleotide encoding the catalytic domain preferably comprises or consists of 58 to 228, 292 to 450, 501 to 590, 663 to 722, 769 to 1043, 1091 to 1766 of SEQ ID NO: 10.

In another embodiment, the present invention also relates to catalytic domain variants of amino acids 20 to 496 of SEQ ID NO: 1 comprising a substitution, deletion, and/or insertion at one or more (e.g., several) positions. In one aspect, the number of amino acid substitutions, deletions and/or insertions introduced into the sequence of amino acids 20 to 496 of SEQ ID NO: 1 is up to 10, e.g., 1, 2, 3, 4, 5, 6, 8, 9, or 10.

Linker Sequence

The linker sequence may be any suitable linker sequence, e.g., a linker sequence derived from an alpha-amylase or a glucoamylase. The linker is preferably a sequence of from about 2 to about 100 amino acid residues, more preferably of from 10 to 50 amino acid residues, such as from 15 to 25 amino acid residues.

In a preferred embodiment, the linker is selected from a polypeptide having at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 2, or from a polypeptide having at least 75%, at least 80%, at least 85%, at least 90%, at least 91%, at least 92%, at least 93%, at least 94%, at least 95%, at least 96%, at least 97%, at least 98%, at least 99% or 100% sequence identity SEQ ID NO: 3.

Carbohydrate-Binding Modules

A carbohydrate-binding module (CBM), or as often referred to, a carbohydrate-binding domain (CBD), is a polypeptide amino acid sequence which binds preferentially to a poly- or oligosaccharide (carbohydrate), frequently—but not necessarily exclusively—to a water-insoluble (including crystalline) form thereof.

CBMs derived from starch degrading enzymes are often referred to as starch-binding modules or SBMs which may occur in certain amylolytic enzymes, such as certain glucoamylases (GA), or in enzymes such as cyclodextrin glucanotransferases, or in alpha-amylases). SBMs are often referred to as SBDs (Starch Binding Domains).

CBMs are found as integral parts of large polypeptides or proteins consisting of two or more polypeptide amino acid sequence regions, especially in hydrolytic enzymes (hydrolases) which typically comprise a catalytic module containing the active site for substrate hydrolysis and a carbohydrate-binding module (CBM) for binding to the carbohydrate substrate in question. Such enzymes can comprise more than one catalytic module and one, two or three CBMs and optionally further comprise one or more polypeptide amino acid sequence regions linking the CBM(s) with the catalytic module(s), a region of the latter type usually being denoted a "linker". Examples of hydrolytic enzymes comprising a CBM—some of which have already been mentioned above—are cellulases, xylanases, mannanases, arabinofuranosidases, acetylesterases and chitinases.

In proteins/polypeptides in which CBMs occur (e.g., enzymes, typically hydrolytic enzymes), a CBM may be located at the N or C terminus or at an internal position.

That part of a polypeptide or protein (e.g., hydrolytic enzyme) which constitutes a CBM per se typically consists of more than about 30 and less than about 250 amino acid residues.

The "Carbohydrate-Binding Module of Family 20" or a CBM-20 module is in the context of this invention defined as a sequence of approximately 100 amino acids having at least 45% homology to the Carbohydrate-Binding Module (CBM) of the polypeptide disclosed in FIG. 1 by Joergensen et al. (1997) in Biotechnol. Lett. 19:1027-1031. The CBM comprises the last 102 amino acids of the polypeptide, i.e., the subsequence from amino acid 582 to amino acid 683. The numbering of Glycoside Hydrolase Families applied in this disclosure follows the concept of Coutinho, P. M. & Henrissat, B. (1999) *CAZy—Carbohydrate Active Enzymes server* at URL: http://afmb.cnrs-mrs.fr/~cazy/CAZY/index.html or alternatively Coutinho, P. M. & Henrissat, B. 1999; The modular structure of cellulases and other carbohydrate-active enzymes: an integrated database approach. In "*Genetics, Biochemistry and Ecology of Cellulose Degradation*", K. Ohmiya, K. Hayashi, K. Sakka, Y. Kobayashi, S. Karita and T. Kimura eds., Uni Publishers Co., Tokyo, pp. 15-23 and Bourne, Y. & Henrissat, B. 2001; Glycoside hydrolases and glycosyltransferases: families and functional modules, *Current Opinion in Structural Biology* 11:593-600.

Examples of enzymes which comprise a CBM suitable for use in the context of the invention are alpha-amylases, maltogenic alpha-amylases, cellulases, xylanases, mannanases, arabinofuranosidases, acetylesterases and chitinases. Further CBMs of interest in relation to the present invention include CBMs deriving from glucoamylases (EC 3.2.1.3) or from CGTases (EC 2.4.1.19).

CBMs deriving from fungal, bacterial or plant sources will generally be suitable for use in the hybrid of the invention. Preferred are CBMs of fungal origin. In this connection, techniques suitable for isolating the relevant genes are well known in the art.

Preferred are hybrids comprising a CBM of Carbohydrate-Binding Module Family 20, 21 or 25, preferably family 20, such as a CBM selected from a polypeptide having at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 4, SEQ ID NO: 5, or SEQ ID NO: 6.

Sources of Polypeptides Having alpha-amylase Activity

A polypeptide having alpha-amylase activity of the present invention may be obtained from a fungus of the genus *Acidomyces*. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one aspect, the polypeptide is a *Acidomyces* polypeptide, e.g., a polypeptide obtained from *Acidomyces acidothermus*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and *Agricultural Research* Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a hybrid polypeptide having alpha-amylase activity, or a catalytic domain having alpha-amylase activity of the present invention, as described herein. In an embodiment, the polynucleotide encoding the hybrid polypeptide, or catalytic domain of the present invention has been isolated.

In one particular embodiment the polynucleotides are selected from:

a) a polynucleotide having at least 75%, at least 80%, at least 85%, at least 90%, at least 91%, at least 92%, at least 93%, at least 94%, at least 95%, at least 96%, at least 97%, at least 98%, at least 99% or 100% sequence identity to nucleotides 58 to 228, 292 to 450, 501 to 590, 663 to 722, 769 to 1043, 1091 to 1766 of SEQ ID NO: 10;

b) a polynucleotide having at least 75%, at least 80%, at least 85%, at least 90%, at least 91%, at least 92%, at least 93%, at least 94%, at least 95%, at least 96%, at least 97%, at least 98%, at least 99% or 100% sequence identity to nucleotides 58 to 228, 292 to 450, 501 to 590, 663 to 722, 769 to 1043, 1091 to 2201 of SEQ ID NO: 22;

c) a polynucleotide having at least 75%, at least 80%, at least 85%, at least 90%, at least 91%, at least 92%, at least 93%, at least 94%, at least 95%, at least 96%, at least 97%, at least 98%, at least 99% or 100% sequence identity to nucleotides 64 to 1920 of SEQ ID NO: 23;

d) c) a polynucleotide having at least 75%, at least 80%, at least 85%, at least 90%, at least 91%, at least 92%, at least 93%, at least 94%, at least 95%, at least 96%, at least 97%, at least 98%, at least 99% or 100% sequence identity to nucleotides 64 to 1923 of SEQ ID NO: 24.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application, Academic Press*, New York. Other nucleic acid amplification procedures such as ligase chain reaction (LCR), ligation activated transcription (LAT) and polynucleotide-based amplification (NASBA) may be used. The polynucleotides may be cloned from a strain of *Acidomyces*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences. In one embodiment, the one or more control sequences are heterologous to the polynucleotide of the present invention.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* those phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. In one embodiment, the one or more control sequences are heterologous to the polynucleotide of the present invention. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. In one embodiment, the one or more control sequences are heterologous to the polynucleotide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the *Fungi Imperfecti* (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No. 9*, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis,*

*Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present disclosure also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Acidomyces* cell. In another aspect, the cell is a *Acidomyces acidothermus* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Production in Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems.

Plant cells and specific plant cell compartments, such as chloroplasts, apoplasts, mitochondria, vacuoles, peroxisomes and cytoplasm are also considered to be a plant part.

Also included within the scope of the present invention are the progeny of such plants, plant parts, and plant cells.

The transgenic plant or plant cell expressing the polypeptide or domain may be constructed in accordance with methods known in the art.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide of the present invention. Preferably, the compositions are enriched in such a polypeptide. The term "enriched" indicates that the alpha-amylase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase. In a particular embodiment, the composition comprises the alpha-amylase of the invention and a glucoamylase.

In an embodiment, the glucoamylase comprised in the composition is of fungal origin, preferably from a stain of *Aspergillus*, preferably *A. niger*, *A. awamori*, or *A. oryzae*; or a strain of *Trichoderma*, preferably *T. reesei*; or a strain of *Talaromyces*, preferably *T. emersonii* or a strain of *Trametes*, preferably *T. cingulata*, or a strain of *Pycnoporus*, preferable *P. sanguineus*, or a strain of *Gloeophyllum*, such as *G. serpiarium* or *G. trabeum*, or a strain of the *Nigrofomes*.

In an embodiment the glucoamylase is derived from *Trametes*, such as a strain of *Trametes cingulata*, such as the one shown in SEQ ID NO: 11 herein.

In an embodiment the glucoamylase is selected from the group consisting of:

(i) a glucoamylase comprising the polypeptide of SEQ ID NO: 11 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 11 herein.

In an embodiment the glucoamylase is derived from *Talaromyces*, such as a strain of *Talaromyces emersonii*, such as the one shown in SEQ ID NO: 12 herein.

In an embodiment the glucoamylase is selected from the group consisting of:

(i) a glucoamylase comprising the polypeptide of SEQ ID NO: 12 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 12 herein.

In an embodiment the glucoamylase is derived from a strain of the genus *Pycnoporus*, in particular a strain of *Pycnoporus sanguineus* described in WO 2011/066576 (SEQ ID NOs 2, 4 or 6), such as the one shown as SEQ ID NO: 4 in WO 2011/066576, or SEQ ID NO: 13 herein.

In an embodiment the glucoamylase is selected from the group consisting of:
(i) a glucoamylase comprising the polypeptide of SEQ ID NO: 13 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at SEQ ID NO: 13 herein.

In an embodiment the glucoamylase is derived from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is the *Gloeophyllum sepiarium* shown in SEQ ID NO: 2 in WO 2011/068803 or SEQ ID NO: 14 herein.

In an embodiment the glucoamylase is derived from *Gloeophyllum serpiarium*, such as the one shown in SEQ ID NO: 14 herein. In an embodiment the glucoamylase is selected from the group consisting of:
(i) a glucoamylase comprising the polypeptide of SEQ ID NO: 14 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 14 herein.

In another embodiment the glucoamylase is derived from *Gloeophyllum trabeum* such as the one shown in SEQ ID NO: 15 herein. In an embodiment the glucoamylase is selected from the group consisting of:
(i) a glucoamylase comprising the polypeptide of SEQ ID NO: 15 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 15 herein.

In an embodiment the glucoamylase is derived from a strain of the genus *Nigrofomes*, in particular a strain of *Nigrofomes* sp. disclosed in WO 2012/064351.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL and AMG™ E (from Novozymes NS); OPTIDEX™ 300, GC480, GC417 (from DuPont); AMIGASE™ and AMIGASE™ PLUS (from DSM); G-ZYME™ G900, G-ZYME™ and G990 ZR (from DuPont).

In addition to a glucoamylase the composition may further comprise a protease. In particular an endoprotease of family S53, more particular an S53 protease derived from *Meripilus giganteus*.

In a preferred embodiment, the ratio between glucoamylase and alpha-amylase present and/or added during saccharification and/or fermentation may preferably be in the range from 500:1 to 1:1, such as from 250:1 to 1:1, such as from 100:1 to 1:1, such as from 100:2 to 100:50, such as from 100:3 to 100:70.

The compositions may be prepared in accordance with methods known in the art and may be in the form of a liquid or a dry composition. For instance, the composition may be in the form of granulate or microgranulate. The variant may be stabilized in accordance with methods known in the art.

The compositions may be prepared in accordance with methods known in the art and may be in the form of a liquid or a dry composition. The compositions may be stabilized in accordance with methods known in the art.

The enzyme composition of the present invention may be in any form suitable for use, such as, for example, a crude fermentation broth with or without cells removed, a cell lysate with or without cellular debris, a semi-purified or purified enzyme composition, or a host cell, as a source of the enzymes.

The enzyme composition may be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

Examples are given below of preferred uses of the compositions of the present invention. The dosage of the composition and other conditions under which the composition is used may be determined on the basis of methods known in the art.

Methods of Using the (Hybrid) Alpha-Amylase of the Invention—Industrial Applications The alpha-amylases of the present invention possess valuable properties allowing for a variety of industrial applications. In particular, the alpha-amylases may be used in ethanol production, and starch conversion processes.

Further, the alpha-amylases of the invention are particularly useful in the production of sweeteners/syrups and ethanol (see, e.g., U.S. Pat. No. 5,231,017), such as fuel, drinking and industrial ethanol, from starch or whole grains.

In one embodiment, the present invention relates to a use of the alpha-amylase according to the invention in a saccharification process, particularly a simultaneous saccharification and fermentation process.

Starch Processing

Native starch consists of microscopic granules, which are insoluble in water at room temperature. When aqueous starch slurry is heated, the granules swell and eventually burst, dispersing the starch molecules into the solution. At temperatures up to about 50° C. to 75° C. the swelling may be reversible. However, with higher temperatures an irreversible swelling called "gelatinization" begins. During this "gelatinization" process there is a dramatic increase in viscosity. Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. In dry milling whole kernels are milled and used. Wet milling gives a good separation of germ and meal (starch granules and protein) and is often applied at locations where the starch hydrolyzate is used in the production of, e.g., syrups. Both dry and wet milling is well known in the art of starch processing and may be used in a process of the invention. Methods for reducing the particle size of the starch containing material are well known to those skilled in the art.

As the solids level is 30-40% in a typical industrial process, the starch has to be thinned or "liquefied" so that it can be suitably processed. This reduction in viscosity is primarily attained by enzymatic degradation in current commercial practice.

Liquefaction is carried out in the presence of an alpha-amylase, preferably a bacterial alpha-amylase and/or acid fungal alpha-amylase. In an embodiment, a phytase is also present during liquefaction. In an embodiment, viscosity reducing enzymes such as a xylanase and/or beta-glucanase is also present during liquefaction.

During liquefaction, the long-chained starch is degraded into branched and linear shorter units (maltodextrins) by an alpha-amylase. Liquefaction may be carried out as a three-step hot slurry process. The slurry is heated to between 60-95° C. (e.g., 70-90° C., such as 77-86° C., 80-85° C., 83-85° C.) and an alpha-amylase is added to initiate liquefaction (thinning).

The slurry may in an embodiment be jet-cooked at between 95-140° C., e.g., 105-125° C., for about 1-15 minutes, e.g., about 3-10 minutes, especially around 5 minutes. The slurry is then cooled to 60-95° C. and more alpha-amylase is added to obtain final hydrolysis (secondary liquefaction). The jet-cooking process is carried out at pH 4.5-6.5, typically at a pH between 5 and 6. The alpha-amylase may be added as a single dose, e.g., before jet cooking.

The liquefaction process is carried out at between 70-95° C., such as 80-90° C., such as around 85° C., for about 10 minutes to 5 hours, typically for 1-2 hours. The pH is between 4 and 7, such as between 5.5 and 6.2. In order to ensure optimal enzyme stability under these conditions, calcium may optionally be added (to provide 1-60 ppm free calcium ions, such as about 40 ppm free calcium ions). After such treatment, the liquefied starch will typically have a "dextrose equivalent" (DE) of 10-16.

Generally liquefaction and liquefaction conditions are well known in the art.

Alpha-amylases for use in liquefaction are preferably bacterial acid stable alpha-amylases. Particularly the alpha-amylase is from an *Exiguobacterium* sp. or a *Bacillus* sp. such as e.g., *Bacillus stearothermophilus* or *Bacillus licheniformis*.

In an embodiment the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 16 herein.

In an embodiment the *Bacillus stearothermophilus* alpha-amylase has a double deletion of two amino acids in the region from position 179 to 182, more particularly a double deletion at positions I181+G182, R179+G180, G180+I181, R179+I181, or G180+G182, preferably I181+G182, and optionally a N193F substitution, (using SEQ ID NO: 16 for numbering).

In an embodiment the *Bacillus stearothermophilus* alpha-amylase has a substitution at position S242, preferably S242Q substitution.

In an embodiment the *Bacillus stearothermophilus* alpha-amylase has a substitution at position E188, preferably E188P substitution.

In an embodiment the alpha-amylase is selected from the group of *Bacillus stearothermophilus* alpha-amylase variants with the following mutations:

I181*+G182*+N193F+E129V+K177L+R179E;

I181*+FG182*+N193F+V59A+Q89R+E129V+K177L+ R179E+H208Y+K220P+N224L+Q254S;

I181*+G182*+N193F+V59A Q89R+E129V+K177L+ R179E+Q254S+M284V; and

I181*+G182*+N193F+E129V+K177L+R179E+K220P+ N224L+S242Q+Q254S (using SEQ ID NO: 16 for numbering).

In an embodiment the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 16.

It should be understood that when referring to *Bacillus stearothermophilus* alpha-amylase and variants thereof they are normally produced in truncated form. In particular, the truncation may be so that the *Bacillus stearothermophilus* alpha-amylase shown in SEQ ID NO: 3 in WO 99/19467 or SEQ ID NO: 16 herein, or variants thereof, are truncated in the C-terminal preferably to have around 490 amino acids, such as from 482-493 amino acids. Preferably the *Bacillus stearothermophilus* variant alpha-amylase is truncated, preferably after position 484 of SEQ ID NO: 16, particularly after position 485, particularly after position 486, particularly after position 487, particularly after position 488, particularly after position 489, particularly after position 490, particularly after position 491, particularly after position 492, more particularly after position 493.

Saccharification may be carried out using conditions well-known in the art with a carbohydrate-source generating enzyme, in particular an alpha-amylase according to the present invention and a glucoamylase. For instance, a full saccharification step may last from about 24 to about 72 hours. However, it is common to do a pre-saccharification of typically 40-90 minutes at a temperature between 30-65° C., typically about 60° C., followed by complete saccharification during fermentation in a simultaneous saccharification and fermentation (SSF) process. Saccharification is typically carried out at a temperature in the range of 20-75° C., e.g., 25-65° C. and 40-70° C., typically around 60° C., and at a pH between about 4 and 5, normally at about pH 4.5.

The saccharification and fermentation steps may be carried out either sequentially or simultaneously. In an embodiment, saccharification and fermentation are performed simultaneously (referred to as "SSF"). However, it is common to perform a pre-saccharification step for about 30 minutes to 2 hours (e.g., 30 to 90 minutes) at a temperature of 30 to 65° C., typically around 60° C. which is followed by a complete saccharification during fermentation referred to as simultaneous saccharification and fermentation (SSF). The pH is usually between 4.2-4.8, e.g., pH 4.5. In a simultaneous saccharification and fermentation (SSF) process, there is no holding stage for saccharification, rather, the yeast and enzymes are added together.

In a typical saccharification process, maltodextrins produced during liquefaction are converted into dextrose by adding a glucoamylase and optionally a debranching enzyme, such as an isoamylase (U.S. Pat. No. 4,335,208) or a pullulanase. The temperature is lowered to 60° C., prior to the addition of the glucoamylase and debranching enzyme. The saccharification process proceeds for 24-72 hours. Prior to addition of the saccharifying enzymes, the pH is reduced to below 4.5, while maintaining a high temperature (above 95° C.), to inactivate the liquefying alpha-amylase. This process reduces the formation of short oligosaccharide called "panose precursors," which cannot be hydrolyzed properly by the debranching enzyme. Normally, about 0.2-0.5% of the saccharification product is the branched trisaccharide panose (Glc p$\alpha$1-6Glc p$\alpha$1-4Glc), which cannot be degraded by a pullulanase. If active amylase from the liquefaction remains present during saccharification (i.e., no denaturing), the amount of panose can be as high as 1-2%, which is highly undesirable since it lowers the saccharification yield significantly.

Other fermentation products may be fermented at conditions and temperatures well known to persons skilled in the art, suitable for the fermenting organism in question.

The fermentation product may be recovered by methods well known in the art, e.g., by distillation.

In a particular embodiment, the process of the invention further comprises, prior to the conversion of a starch-containing material to sugars/dextrins the steps of:

(x) reducing the particle size of the starch-containing material; and (y) forming a slurry comprising the starch-containing material and water.

In an embodiment, the starch-containing material is milled to reduce the particle size. In an embodiment the particle size is reduced to between 0.05-3.0 mm, preferably 0.1-0.5 mm, or so that at least 30%, preferably at least 50%, more preferably at least 70%, even more preferably at least 90% of the starch-containing material fits through a sieve with a 0.05-3.0 mm screen, preferably 0.1-0.5 mm screen.

The aqueous slurry may contain from 10-55 wt. % dry solids (DS), preferably 25-45 wt. % dry solids (DS), more preferably 30-40 wt. % dry solids (DS) of starch-containing material.

Conventional starch-conversion processes, such as liquefaction and saccharification processes are described, e.g., in U.S. Pat. No. 3,912,590, EP 252730 and EP 063909.

In an embodiment, the conversion process degrading starch to lower molecular weight carbohydrate components such as sugars or fat replacers includes a debranching step.

In the case of converting starch into a sugar, the starch is depolymerized. Such a depolymerization process consists of, e.g., a pre-treatment step and two or three consecutive process steps, i.e., a liquefaction process, a saccharification process, and depending on the desired end-product, an optional isomerization process.

When the desired final sugar product is, e.g., high fructose syrup the dextrose syrup may be converted into fructose. After the saccharification process, the pH is increased to a value in the range of 6-8, e.g., pH 7.5, and the calcium is removed by ion exchange. The dextrose syrup is then converted into high fructose syrup using, e.g., an immobilized glucose isomerase.

Production of Fermentation Products

Fermentable sugars (e.g., dextrins, monosaccharides, particularly glucose) are produced from enzymatic saccharification. These fermentable sugars may be further purified and/or converted to useful sugar products. In addition, the sugars may be used as a fermentation feedstock in a microbial fermentation process for producing end-products, such as alcohol (e.g., ethanol, and butanol), organic acids (e.g., succinic acid, 3-HP and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof).

In an embodiment, the fermentable sugars obtained during the liquefaction process steps are used to produce alcohol and particularly ethanol. In ethanol production, an SSF process is commonly used wherein the saccharifying enzymes and fermenting organisms (e.g., yeast) are added together and then carried out at a temperature of 30-40° C.

The organism used in fermentation will depend on the desired end-product. Typically, if ethanol is the desired end product yeast will be used as the fermenting organism. In some preferred embodiments, the ethanol-producing microorganism is a yeast and specifically *Saccharomyces* such as strains of *S. cerevisiae* (U.S. Pat. No. 4,316,956). A variety of *S. cerevisiae* are commercially available and these include but are not limited to FALI (Fleischmann's Yeast), SUPERSTART (Alltech), FERMIOL (DSM Specialties), RED STAR (Lesaffre) and Angel alcohol yeast (Angel Yeast Company, China). The amount of starter yeast employed in the methods is an amount effective to produce a commercially significant amount of ethanol in a suitable amount of time, (e.g., to produce at least 10% ethanol from a substrate having between 25-40% DS in less than 72 hours). Yeast cells are generally supplied in amounts of about $10^4$ to about $10^{12}$, and preferably from about $10^7$ to about $10^{10}$ viable yeast count per mL of fermentation broth. After yeast is added to the mash, it is typically subjected to fermentation for about 24-96 hours, e.g., 35-60 hours. The temperature is between about 26-34° C., typically at about 32° C., and the pH is from pH 3-6, e.g., around pH 4-5.

The fermentation may include, in addition to a fermenting microorganisms (e.g., yeast), nutrients, and additional enzymes, including phytases. The use of yeast in fermentation is well known in the art.

In further embodiments, use of appropriate fermenting microorganisms, as is known in the art, can result in fermentation end product including, e.g., glycerol, 1,3-propanediol, gluconate, 2-keto-D-gluconate, 2,5-diketo-D-gluconate, 2-keto-L-gulonic acid, succinic acid, lactic acid, amino acids, and derivatives thereof. More specifically when lactic acid is the desired end product, a *Lactobacillus* sp. (*L. casei*) may be used; when glycerol or 1,3-propanediol are the desired end-products *E. coli* may be used; and when 2-keto-D-gluconate, 2,5-diketo-D-gluconate, and 2-keto-L-gulonic acid are the desired end products, *Pantoea citrea* may be used as the fermenting microorganism. The above enumerated list are only examples and one skilled in the art will be aware of a number of fermenting microorganisms that may be used to obtain a desired end product.

Processes for Producing Fermentation Products from Un-Gelatinized Starch-Containing Material The invention relates to processes for producing fermentation products from starch-containing material without gelatinization (i.e., without cooking) of the starch-containing material (often referred to as a "raw starch hydrolysis" process). The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of an alpha-amylase of the invention and carbohydrate-source generating enzyme(s) to produce sugars that can be fermented into the fermentation product by a suitable fermenting organism. In this embodiment the desired fermentation product, e.g., ethanol, is produced from un-gelatinized (i.e., uncooked), preferably milled, cereal grains, such as corn.

Accordingly, in one aspect the invention relates to processes for producing a fermentation product from starch-containing material comprising simultaneously saccharifying and fermenting starch-containing material using a carbohydrate-source generating enzymes and a fermenting organism at a temperature below the initial gelatinization temperature of said starch-containing material in the presence of an alpha-amylase of the invention.

Saccharification and fermentation may also be separate. Thus, in another aspect the invention relates to processes of producing fermentation products, comprising the following steps:

(i) saccharifying a raw starch-containing material at a temperature below the initial gelatinization temperature; and (ii) fermenting using a fermentation organism;

wherein step (i) is carried out using at least an alpha-amylase of the invention, and optionally a glucoamylase.

In one embodiment, the fermenting organism expresses the alpha-amylase of the invention and/or a glucoamylase.

The fermentation product, e.g., ethanol, may optionally be recovered after fermentation, e.g., by distillation. Typically, amylase(s), such as glucoamylase(s) and/or other carbohydrate-source generating enzymes, and/or alpha-amylase(s), is(are) present during fermentation. Examples of glucoamylases and other carbohydrate-source generating enzymes include raw starch hydrolyzing glucoamylases. Examples of alpha-amylase(s) include acid alpha-amylases such as acid fungal alpha-amylases, particularly the alpha-amylase of the invention. Examples of fermenting organisms include yeast, e.g., a strain of *Saccharomyces cerevisiae*. The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, *Starch/Stärke* 44(12): 461-466. Before initiating the process, a slurry of starch-containing material, such as granular starch, having 10-55 w/w % dry solids (DS), preferably 25-45 w/w % dry solids, more preferably 30-40 w/w % dry solids of starch-containing material may be prepared. The slurry may include water and/or process waters, such as stillage (backset), scrubber water, evaporator condensate or distillate, side-stripper water from distillation, or process water from other fermentation product plants. Because the process of the invention is carried out below the initial gelatinization temperature, and thus no significant viscosity increase takes place, high levels of stillage may be used if desired. In an embodiment the aqueous slurry contains from about 1 to about 70 vol. %, preferably 15-60 vol. %, especially from about 30 to 50 vol. % water and/or process waters, such as stillage (backset), scrubber water, evaporator condensate or distillate, side-stripper water from distillation, or process water from other fermentation product plants, or combinations thereof, or the like. The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material are converted into a soluble starch hydrolyzate. A process in this aspect of the invention is conducted at a temperature below the initial gelatinization temperature, which means that the temperature typically lies in the range between 30–75° C., preferably between 45-60° C. In a preferred embodiment the process carried at a temperature from 25° C. to 40° C., such as from 28° C. to 35° C., such as from 30° C. to 34° C., preferably around 32° C. In an embodiment the process is carried out so that the sugar level, such as glucose level, is kept at a low level, such as below 6 w/w %, such as below about 3 w/w %, such as below about 2 w/w %, such as below about 1 w/w %, such as below about 0.5 w/w %, or below 0.25 w/w %, such as below about 0.1 w/w %. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 w/w %, such as below about 0.2 w/w %. The process of the invention may be carried out at a pH from about 3 and 7, preferably from pH 3.5 to 6, or more preferably from pH 4 to 5. In an embodiment fermentation is ongoing for 6 to 120 hours, in particular 24 to 96 hours.

Processes for Producing Fermentation Products from Gelatinized Starch-Containing Material In this aspect, the invention relates to processes for producing fermentation products, especially ethanol, from starch-containing material, which process includes a liquefaction step and sequentially or simultaneously performed saccharification and fermentation steps. Consequently, the invention relates to processes for producing fermentation products from starch-containing material comprising the steps of:

(a) liquefying starch-containing material at a temperature above the initial gelatinization temperature in the presence of an alpha-amylase;

(b) saccharifying the liquefied material obtained in step (a) using an alpha-amylase of the invention, and optionally a glucoamylase; and (c) fermenting using a fermenting organism.

In an embodiment, a protease, such as a themo-stable serine protease, an acid fungal protease or a metallo protease is added before, during and/or after liquefaction. In an embodiment the metalloprotease is derived from a strain of *Thermoascus*, e.g., a strain of *Thermoascus aurantiacus*, especially *Thermoascus aurantiacus* CGMCC No. 0670. In another embodiment the protease is a bacterial protease, particularly a serine protease, e.g., an S8 protease, more particularly a protease derived from a strain of *Pyrococcus* or *Thermococcus*, more particularly from *Pyrococcus furiosus* disclosed in U.S. Pat. No. 6,358,726, or SEQ ID NO: 17 herein.

In an embodiment the glucoamylase is derived from a strain of *Aspergillus*, e.g., *Aspergillus niger* or *Aspergillus awamori*, a strain of *Talaromyces*, especially *Talaromyces*

*emersonii*; or a strain of *Athelia*, especially *Athelia rolfsii*; a strain of *Trametes*, e.g., *Trametes cingulata*; or a strain of *Pycnoporus*, or a strain of *Gloeophyllum*, such as *G. serpiarium* or *G. trabeum*, or a strain of the *Nigrofomes*; or a mixture thereof. Saccharification step (b) and fermentation step (c) may be carried out either sequentially or simultaneously. A pullulanase and/or protease may be added during saccharification and/or fermentation when the process is carried out as a sequential saccharification and fermentation process and before or during fermentation when steps (b) and (c) are carried out simultaneously (SSF process). The pullulanase and/or protease may also advantageously be added before liquefaction (pre-liquefaction treatment), i.e., before or during step (a), and/or after liquefaction (post liquefaction treatment), i.e., after step (a). The pullulanase is most advantageously added before or during liquefaction, i.e., before or during step (a). The fermentation product, such as especially ethanol, may optionally be recovered after fermentation, e.g., by distillation. The fermenting organism is preferably yeast, preferably a strain of *Saccharomyces cerevisiae*. In a preferred embodiment, the yeast is expressing the variant glucoamylase of the invention. In a particular embodiment, the process of the invention further comprises, prior to step (a), the steps of:

x) reducing the particle size of the starch-containing material, preferably by milling (e.g., using a hammer mill);

y) forming a slurry comprising the starch-containing material and water.

In an embodiment, the particle size is smaller than a #7 screen, e.g., a #6 screen. A #7 screen is usually used in conventional prior art processes. The aqueous slurry may contain from 10-55, e.g., 25-45 and 30-40, w/w % dry solids (DS) of starch-containing material. The slurry is heated to above the gelatinization temperature and an alpha-amylase variant may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C. at pH 4-6, preferably 4.5-5.5, and alpha-amylase variant, optionally together with a pullulanase and/or protease, preferably metalloprotease, are added to initiate liquefaction (thinning). In an embodiment the slurry may then be jet-cooked at a temperature between 95-140° C., preferably 100-135° C., such as 105-125° C., for about 1-15 minutes, preferably for about 3-10 minutes, especially around about 5 minutes. The slurry is cooled to 60-95° C. and more alpha-amylase and optionally pullulanase and/or protease, preferably metalloprotease, is(are) added to finalize hydrolysis (secondary liquefaction). The liquefaction process is usually carried out at pH 4.5-6.5, such as around 4.8, or a pH between 5.0-6.2, such as 5.0-6.0, such as between 5.0-5.5, such as around 5.2, such as around 5.4, such as around 5.6, such as around 5.8. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 20-75° C., preferably from 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 36° C., such as from 30° C. to 34° C., preferably around about 32° C. In an embodiment fermentation is ongoing for 6 to 120 hours, in particular 24 to 96 hours.

Processes for Producing Syrup from Geleatinized Starch-Containing Material

In this aspect the fermentation step is left out, however, conditions are generally as described above for "Processes for producing fermentation products from gelatinized starch-containing material". Thus, in this aspect the present invention relates to a process for producing a syrup from starch-containing material comprising the steps of:

a) liquefying the starch-containing material at a temperature above the initial gelatinization temperature in the presence of an alpha-amylase; and b) saccharifying the product of step a) in the presence of a glucoamylase and an alpha-amylase of the invention.

Protease Present and/or Added During Liquefaction

According to the invention a thermostable protease may in one embodiment be present and/or added during liquefaction together with an alpha-amylase, such as a thermostable alpha-amylase, and optionally a carbohydrate-source generating enzyme, in particular a thermostable glucoamylase or thermostable pullulanase.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

There are no limitations on the origin of the protease used in a process of the invention as long as it fulfills the thermostability properties defined below.

The protease may be a variant of, e.g., a wild-type protease as long as the protease has the thermostability properties defined herein.

In an embodiment the protease has a thermostability above 60%, such as above 90%, such as above 100%, such as above 110% at 85° C. as determined using the Zein-BCA assay.

In an embodiment protease has a thermostability between 60-120, such as between 70-120%, such as between 80-120%, such as between 90-120%, such as between 100-120%, such as 110-120% at 85° C. as determined using the Zein-BCA assay.

In one embodiment the thermostable protease is a variant of a metallo protease as defined above. In an embodiment the thermostable protease used in a process of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In an preferred embodiment the thermostable protease is a variant of the metallo protease disclosed as the mature part of SEQ ID NO: 2 disclosed in WO 2003/048353 or the mature part of SEQ ID NO: 1 in WO 2010/008841 with the following mutations:
D79L+S87P+A112P+D142L;
D79L+S87P+D142L; or
A27K+D79L+Y82F+S87G+D104P+A112P+A126V+D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841.

The thermostable protease may also be derived from a bacterium, particularly a serine protease, more particularly an S8 protease, more particularly an S8 protease from *Pyrococcus* sp or *Thermococcus* sp.

In an embodiment the thermostable protease is derived from a strain of the bacterium *Pyrococcus*, such as a strain of *Pyrococcus furiosus* (pfu protease).

In an embodiment the protease is one shown as SEQ ID NO: 1 in U.S. Pat. No. 6,358,726-B1 (Takara Shuzo Company) and SEQ ID NO: 17 herein.

In another embodiment the thermostable protease is one disclosed in SEQ ID NO: 17 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 17 herein.

Glucoamylase Present and/or Added in Liquefaction

In an embodiment a glucoamylase is present and/or added in liquefaction step a) in a process of the invention (i.e., oil recovery process and fermentation product production process).

In a preferred embodiment the glucoamylase present and/or added in liquefaction step a) is derived from a strain of the genus *Penicillium*, especially a strain of *Penicillium oxalicum* disclosed as SEQ ID NO: 2 in WO 2011/127802 or SEQ ID NO: 18 herein.

In an embodiment the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NO: 18 herein.

In a preferred embodiment the glucoamylase is a variant of the *Penicillium oxalicum* glucoamylase shown in SEQ ID NO: 2 in WO 2011/127802 or SEQ ID NO: 18 herein having a K79V substitution (using the mature sequence shown in SEQ ID NO: 18 for numbering), such as a variant disclosed in WO 2013/053801.

In a preferred embodiment the glucoamylase present and/or added in liquefaction is the *Penicillium oxalicum* glucoamylase having a K79V substitution and preferably further one of the following substitutions:
P11F+T65A+Q327F;
P2N+P4S+P11F+T65A+Q327F (using SEQ ID NO: 18 for numbering).

In an embodiment the glucoamylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 18 herein.

The glucoamylase may be added in amounts from 0.1-100 micro grams EP/g, such as 0.5-50 micro grams EP/g, such as 1-25 micrograms EP/g, such as 2-12 micrograms EP/g DS.

Glucoamylase Present and/or Added in Saccharification and/or Fermentation

A glucoamylase is present and/or added in saccharification and/or fermentation, preferably simultaneous saccharification and fermentation (SSF), in a process of the invention (i.e., oil recovery process and fermentation product production process).

In an embodiment the glucoamylase present and/or added in saccharification and/or fermentation is of fungal origin, preferably from a stain of *Aspergillus*, preferably *A. niger*, *A. awamori*, or *A. oryzae*; or a strain of *Trichoderma*, preferably *T. reesei*; or a strain of *Talaromyces*, preferably *T. emersonii* or a strain of *Trametes*, preferably *T. cingulata*, or a strain of *Pycnoporus*, or a strain of *Gloeophyllum*, such as *G. serpiarium* or *G. trabeum*, or a strain of the *Nigrofomes*.

In an embodiment the glucoamylase is derived from *Talaromyces*, such as a strain of *Talaromyces emersonii*, such as the one shown in SEQ ID NO: 12 herein, In an embodiment the glucoamylase is selected from the group consisting of:
(i) a glucoamylase comprising the polypeptide of SEQ ID NO: 12 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 12 herein.

In an embodiment the glucoamylase is derived from a strain of the genus *Pycnoporus*, in particular a strain of *Pycnoporus sanguineus* described in WO 2011/066576 (SEQ ID NOs 2, 4 or 6), such as the one shown as SEQ ID NO: 4 in WO 2011/066576, or SEQ ID NO: 13 herein. In an embodiment the glucoamylase is derived from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is the *Gloeophyllum sepiarium* shown in SEQ ID NO: 2 in WO 2011/068803 or SEQ ID NO: 14 herein.

In a preferred embodiment the glucoamylase is derived from *Gloeophyllum serpiarium*, such as the one shown in SEQ ID NO: 14 herein. In an embodiment the glucoamylase is selected from the group consisting of:
(i) a glucoamylase comprising the polypeptide of SEQ ID NO: 14 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 14 herein.

In another embodiment the glucoamylase is derived from *Gloeophyllum trabeum* such as the one shown in SEQ ID NO: 15 herein. In an embodiment the glucoamylase is selected from the group consisting of:
(i) a glucoamylase comprising the polypeptide of SEQ ID NO: 15 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 15 herein.

In an embodiment the glucoamylase is derived from a strain of the genus *Nigrofomes*, in particular a strain of *Nigrofomes* sp. disclosed in WO 2012/064351.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL and AMG™ E (from Novozymes NS); OPTIDEX™ 300, GC480, GC417 (from DuPont); AMIGASE™ and AMIGASE™ PLUS (from DSM); G-ZYME™ G900, G-ZYME™ and G990 ZR (from DuPont).

According to a preferred embodiment of the invention the glucoamylase is present and/or added in saccharification and/or fermentation in combination with an alpha-amylase. Examples of suitable alpha-amylase are described below.

Alpha-Amylase Present and/or Added in Saccharification and/or Fermentation

In an embodiment an alpha-amylase of the invention is present and/or added in saccharification and/or fermentation in a process of the invention. In a preferred embodiment the alpha-amylase is of fungal or bacterial origin. In a preferred embodiment the alpha-amylase is a fungal acid stable alpha-amylase of the invention. A fungal acid stable alpha-amylase is an alpha-amylase that has activity in the pH range of 3.0 to 7.0 and preferably in the pH range from 3.5 to 6.5, including activity at a pH of about 4.0, 4.5, 5.0, 5.5, and 6.0.

In a preferred embodiment the alpha-amylase present and/or added in saccharification and/or fermentation is derived from a strain of the genus *Acidomyces*, preferably a strain the *Acidomyces acidothermus*, such as one shown in SEQ ID NO: 1 herein, or a hybrid alpha-amylase according to the invention.

In an embodiment the alpha-amylase present and/or added in saccharification and/or fermentation is selected from the mature alpha-amylase of SEQ ID NO: 1, or a hybrid alpha-amylase of SEQ ID NO: 7, SEQ ID NO: 8 or SEQ ID NO: 9 or an alpha-amylase having at least 80%, at least 85%, at least 90%, at least 91%, at least 92%, at least 93%, at least 94%, at least 95%, at least 96%, at least 97%, at least 98%, at least 99% or 100% identity to amino acids 20 to 494 of SEQ ID NO: 1, or a hybrid alpha-amylase of SEQ ID NO: 7, SEQ ID NO: 8 or SEQ ID NO: 9; or a hybrid alpha-amylase comprising a first polypeptide sequence comprising a catalytic core, a second polypeptide sequence comprising a linker and a third polypeptide sequence comprising a starch binding domain (SBD), wherein
(a) the catalytic core is selected from a polypeptide having at least 80%, at least 85%, at least 90%, at least 91%, at least 92%, at least 93%, at least 94%, at least 95%, at least 96%, at least 97%, at least 98%, at least 99% or 100% identity to amino acids 20 to 494 of SEQ ID NO: 1 or amino acids 20 to 496 of SEQ ID NO: 1;
(b) the linker is selected from a polypeptide having at least 75%, at least 80%, at least 85%, at least 90%, at least 91%, at least 92%, at least 93%, at least 94%, at least 95%, at least 96%, at least 97%, at least 98%, at least 99% or 100% identity to SEQ ID NO: 2 or SEQ ID NO: 3;
(c) the SBD is selected from a polypeptide having at least 75%, at least 80%, at least 85%, at least 90%, at least 91%, at least 92%, at least 93%, at least 94%, at least 95%, at least 96%, at least 97%, at least 98%, at least 99% or 100% identity to SEQ ID NO: 4, SEQ ID NO: 5, and SEQ ID NO: 6.

In a preferred embodiment, the ratio between glucoamylase and alpha-amylase present and/or added during saccharification and/or fermentation may preferably be in the range from 500:1 to 1:1, such as from 250:1 to 1:1, such as from 100:1 to 1:1, such as from 100:2 to 100:50, such as from 100:3 to 100:70.

Fermentation Medium

The environment in which fermentation is carried out is often referred to as the "fermentation media" or "fermentation medium". The fermentation medium includes the fermentation substrate, that is, the carbohydrate source that is metabolized by the fermenting organism. According to the invention the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

The term "fermenting organism" refers to any organism, including bacterial and fungal organisms, especially yeast, suitable for use in a fermentation process and capable of producing the desired fermentation product. Especially suitable fermenting organisms are able to ferment, i.e., convert, sugars, such as glucose or maltose, directly or indirectly into the desired fermentation product, such as ethanol. Examples of fermenting organisms include fungal organisms, such as yeast. Preferred yeast includes strains of *Saccharomyces* spp., in particular, *Saccharomyces cerevisiae*.

Suitable concentrations of the viable fermenting organism during fermentation, such as SSF, are well known in the art or can easily be determined by the skilled person in the art. In one embodiment the fermenting organism, such as ethanol fermenting yeast, (e.g., *Saccharomyces cerevisiae*) is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Examples of commercially available yeast includes, e.g., RED START™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived therefrom, or cereals. Contemplated are also waxy and non-waxy types of corn and barley. In a preferred embodiment the starch-containing material, used for ethanol production according to the invention, is corn or wheat.

Fermentation Products

The term "fermentation product" means a product produced by a process including a fermentation step using a fermenting organism. Fermentation products contemplated according to the invention include alcohols (e.g., ethanol, methanol, butanol; polyols such as glycerol, sorbitol and inositol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferably processes of the invention are used for producing an alcohol, such as ethanol. The fermentation product, such as ethanol, obtained according to the invention, may be used as fuel, which is typically blended with gasoline. However, in the case of ethanol it may also be used as potable ethanol.

Recovery of Fermentation Products

Subsequent to fermentation, or SSF, the fermentation product may be separated from the fermentation medium. The slurry may be distilled to extract the desired fermentation product (e.g., ethanol). Alternatively, the desired fermentation product may be extracted from the fermentation medium by micro or membrane filtration techniques. The fermentation product may also be recovered by stripping or other method well known in the art.

The present invention is further illustrated in the following numbered embodiments:

Embodiment 1. A hybrid polypeptide having alpha-amylase activity, selected from a first polypeptide sequence comprising a catalytic core, and a second polypeptide sequence comprising a carbohydrate binding module (CBM), wherein (a) the catalytic core is selected from a polypeptide having at least 80%, at least 85%, at least 90%, at least 91%, at least 92%, at least 93%, at least 94%, at least 95%, at least 96%, at least 97%, at least 98%, at least 99% or 100% sequence identity to amino acids 20 to 494 of SEQ ID NO: 1 or amino acids 20 to 496 of SEQ ID NO: 1; and
(b) the CBM is selected from a polypeptide having at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 4, SEQ ID NO: 5, or SEQ ID NO: 6.

Embodiment 2. The hybrid alpha-amylase of embodiment 1, further comprising a linker comprising a sequence of from about 2 to about 100 amino acid residues, more preferably from 10 to 50 amino acid residues, such as from 15 to 25 amino acid residues.

Embodiment 3. The hybrid alpha-amylase of embodiment 2, wherein the linker is selected from a polypeptide having at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 2, or SEQ ID NO: 3.

Embodiment 4. The hybrid polypeptide of embodiment 1 selected from a polypeptide having 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 7, SEQ ID NO: 8, or SEQ ID NO: 9.

Embodiment 5. The hybrid polypeptide of any of embodiments 1-4, comprising or consisting of the amino acids of SEQ ID NO: 7, SEQ ID NO: 8, or SEQ ID NO: 9.

Embodiment 6. A polypeptide comprising a catalytic domain selected from the group consisting of:
(a) a catalytic domain having at least 80%, at least 85%, at least 90%, at least 91%, at least 92%, at least 93%, at least 94%, at least 95%, at least 96%, at least 97%, at least 98%, at least 99% or 100% sequence identity to amino acids 20 to 494 of SEQ ID NO: 1 or amino acids 20 to 496 of SEQ ID NO: 1;
(b) a catalytic domain encoded by a polynucleotide having at least 75%, at least 80%, at least 85%, at least 90%, at least 91%, at least 92%, at least 93%, at least 94%, at least 95%, at least 96%, at least 97%, at least 98%, at least 99% or 100% sequence identity to the nucleotides 58 to 228, 292 to 450, 501 to 590, 663 to 722, 769 to 1043, 1091 to 1766 of SEQ ID NO: 10;
(c) a fragment of the catalytic domain of (a), or (b) that has alpha-amylase activity.

Embodiment 7. The polypeptide of embodiment 6, further comprising a carbohydrate binding module.

Embodiment 8. The polypeptide of embodiment 7, wherein the CBM is selected from a CBM Family 20, 21 or 25, particularly Family 20.

Embodiment 9. The polypeptide of any of the embodiments 7-8 further comprising a linker.

Embodiment 10. The polypeptide of embodiment 9, wherein the linker comprises a sequence of from about 2 to about 100 amino acid residues, more preferably from 10 to 50 amino acid residues, such as from 15 to 25 amino acid residues.

Embodiment 11. A composition comprising the polypeptide of any of embodiments 1-10.

Embodiment 12. A whole broth formulation or cell culture composition comprising the polypeptide of any of embodiments 1-10.

Embodiment 13. A use of a polypeptide of any of embodiments 1-10 for production of syrup and/or a fermentation product.

Embodiment 14. A process of producing a fermentation product from starch-containing material comprising the steps of: (a) liquefying starch-containing material above the initial gelatinization temperature of said starch-containing material in the presence of an alpha amylase; (b) saccharifying the liquefied material; and (c) fermenting with a fermenting organism; wherein step (b) is carried out using at least an alpha-amylase of any of embodiments 1-10, and optionally a glucoamylase.

Embodiment 15. The process of embodiment 14, wherein step (b) and step (c) are carried out simultaneously.

Embodiment 16. A process of producing a fermentation product from raw starch material, comprising the steps of: (a) saccharifying starch-containing material at a temperature below the initial gelatinization temperature of said starch-containing material; and (b) fermenting with a fermenting organism, wherein step (a) is carried out using at least an alpha-amylase of any of the embodiments 1-10, and optionally a glucoamylase.

Embodiment 17. A process of producing a syrup product from starch-containing material, comprising the step of: (a) liquefying starch-containing material at a temperature above the initial gelatination temperature of said starch-containing material in the presence of an alpha-amylase; (b) saccharifying the liquefied material in the presence of an alpha-amylase of any of the embodiments 1-10, and optionally a glucoamylase.

Embodiment 18. The process of any of embodiments 16-17, wherein steps a) and b) are carried out simultaneously.

Embodiment 19. A polynucleotide encoding the polypeptide of any of embodiments 1-10.

Embodiment 20. A nucleic acid construct or expression vector comprising the polynucleotide of embodiment 19 operably linked to one or more control sequences that direct the production of the polypeptide in an expression host.

Embodiment 21. A recombinant host cell comprising the polynucleotide of embodiment 19 operably linked to one or more control sequences that direct the production of the polypeptide.

Embodiment 22. The host cell according to embodiment 21, wherein the host cell is a yeast cell, particularly a *Saccharomyces*, such as *Saccharomyces cerevisiae*.

Embodiment 23. The process of any of the embodiments 14-16, wherein the host cell of any of embodiments 21-22 is applied in the fermentation step.

Embodiment 24. The process of embodiment 23, wherein the yeast cell is expressing the alpha-amylase of any of the embodiments 1-10 and a glucoamylase.

Embodiment 25. A method of producing a polypeptide of any of embodiments 1-10, comprising cultivating the host cell of embodiment 21 under conditions conducive for production of the polypeptide.

Embodiment 26. The method of embodiment 25, further comprising recovering the polypeptide.

Embodiment 27. A transgenic plant, plant part or plant cell comprising the polynucleotide of embodiments 19.

The present invention is further described by the following examples that should not be construed as limiting the scope of the invention.

EXAMPLES

Strains

Strain NN070838 (*Acidomyces acidothermus*) was isolated from an environmental sample collected in Kalundborg, Denmark Sep. 10 2015.

Example 1: Raw Starch Degradation Assay

The raw starch degradation performance was measured by the release of glucose from granular starch with a fungal glucoamylase in combination with the hybrid alpha-amylases of the invention. A commercial alpha-amylase was used as control (shown in SEQ ID NO: 19). The purified alpha-amylase was diluted to 0.156 µg/ml by 50 mM acetate buffer (pH 4.0). Thirty microliter of the enzyme solution was transferred into 2.0 ml deep-well plate wells, and 270 µl substrate solution (0.2% raw starch dispersed in 50 mM acetate buffer pH 3.5 or 4.0, 1 mM $CaCl_2$), 1.25 µg/ml fungal glucoamylase (SEQ ID NO: 20), with or without 15% ethanol (v/v)) was added to start the reaction. The substrate suspension was stirred until just before being added. After incubation at 32° C. for 180 min with shaking at 1200 rpm, the samples were centrifuged to spin down residual starch granule and the glucose concentration of the supernatant was measured by mixing 20 µl aliquot with 200 µl commercial glucose oxidase-peroxidase method-based glucose detection solution (Glucose C2 test, Wako Chemical. Co) in which acarbose as a glucoamylase inhibitor had been dissolved to be 0.5 mM prior to use. Absorbance at 505 nm was measured and relative performance was calculated.

| | RSH | RSH w/EtOH | Core | Linker | SBD |
|---|---|---|---|---|---|
| Control AA | 1.00 | 1.00 | Rhizomucor pusillus AA (aa 1-438 of SEQ ID NO: 19) | A. niger AMG (SEQ ID NO: 2) | A. niger AMG (SEQ ID NO: 4) |
| JA308 | 1.05 | 1.16 | Acidomyces acidothermus AA (aa 20-496 of SEQ ID NO: 1) | A. niger AMG (SEQ ID NO: 2) | A. niger AMG (SEQ ID NO: 4) |
| JA503 | 1.20 | 1.41 | Acidomyces acidothermus AA (aa 20-494 of SEQ ID NO: 1) | Bulgaria inquinans GH13 (SEQ ID NO: 3) | Aspergillus ochraceus AMG (SEQ ID NO: 5) |
| JA514 | 1.19 | 1.42 | Acidomyces acidothermus AA (aa 20-494 of SEQ ID NO: 1) | A. niger AMG (SEQ ID NO: 2) | Penicillium sp. AMG (SEQ ID NO: 6) |

Example 2: Prolonged Raw Starch Degradation Assay

Raw starch degradation performance with prolonged incubation time at low pH with or without EtOH was measured by release of glucose from granular starch with a fungal glucoamylase catalytic core in combination with the hybrid alpha-amylases of the invention. A commercial alpha-amylase was used as control (shown in SEQ ID NO: 19). The purified alpha-amylase was diluted to 0.1 mg/ml by 50 mM acetate buffer (pH3.5 and 3.75). Fungal glucoamylase catalytic core domain (SEQ ID NO: 21) was prepared as culture supernatant and diluted to 1 mg/ml. The same volume of alpha-amylase and glucoamylase catalytic core were mixed. Enzyme mix was diluted by three times with 50 mM acetate buffer (pH3.5 and 3.75). Twenty microliter of diluted enzyme mix was transferred into 24-well plate wells, and 980 µl substrate solution (1.5% raw starch dispersed in 50 mM acetate buffer pH 3.5 and 3.75, 1 mM $CaCl_2$), with or without 15% ethanol (v/v)) was added to start the reaction. The substrate solution was stirred until just before being added. After incubation at 32° C. for 18 and 48 hours with shaking at 1200 rpm, samples were centrifuged to spin down residual starch granule and the supernatant was diluted by 15 times with ultra-pure water. Glucose concentration of diluted supernatant was measured by mixing 10 µl aliquot with 200 µl commercial glucose oxidase-peroxidase method-based glucose detection solution (Glucose C2 test, Wako Chemical. Co) in which acarbose as a glucoamylase inhibitor had been dissolved to be 0.5 mM prior to use. Absorbance at 505 nm was measured and relative performance was calculated.

| | | 18 hours | | | | 42 hors | | |
|---|---|---|---|---|---|---|---|---|
| JA | pH 3.5 | pH 3.5 w/EtOH | pH 3.75 | pH 3.75 w/EtOH | pH 3.5 | pH 3.5 w/EtOH | pH 3.75 | pH 3.75 w/EtOH |
| Control AA | 1.0 | 1.0 | 1.0 | 1.0 | 1.0 | 1.0 | 1.0 | 1.0 |
| JA308 | 2.3 | 3.2 | 1.3 | 2.0 | 2.4 | 2.9 | 1.3 | 1.8 |
| JA503 | 1.5 | 2.2 | 1.1 | 1.5 | 1.4 | 2.0 | 1.1 | 1.4 |
| JA514 | 2.2 | 2.5 | 1.2 | 1.8 | 2.3 | 2.5 | 1.2 | 1.7 |

Example 3: Stability Test at Low pH

Enzyme stability at low pH with or without EtOH was evaluated by residual activity after incubation at pH 3.0, 32° C. The purified alpha-amylase was diluted to 0.1 mg/ml by 100 mM glycine-acetate buffer pH 4.0 with 50 mM $CaCl_2$). Ten microliters of diluted enzymes were transferred into PCR tube and mixed with 90 µl of dilution buffer (100 mM glycine-acetate buffer pH3, 50 mM $CaCl_2$), 0.01% triton X-100 with or without 15% EtOH (v/v)). After incubation at 32° C. for 0, 3 or 20 hours, 10 µl of samples were transferred into 96-well plate and mixed with 90 µl of 50 mM NaOAc (pH4.0). Twenty microliters of diluted samples were transferred into new 96-well palate and mixed with 60 µl of 1:1 mixture of substrate solution and enzyme solution of commercial alpha-amylase colorimetric assay kit (Kikkoman Biochemifa Company) using synthetic substrate (2-chloro-4-nitrophenyl 65-azido-65-deoxy-β-maltopentaoside, N3-G5-β-CNP). After incubation at room temperature for 30 minutes, 120 µl of stop solution (CaCO2) was added. Absorbance at 405 nm was measured and residual activity was calculated. The residual activity was measured for the core alpha-amylase according to the invention as well as the hybrid alpha-amylases of the invention. A prior art alpha-amylase (SEQ ID NO: 19) was included as control.

Residual Activity after Low pH Incubation (3 Hrs and 20 Hrs)

| | 3 hr | | | | | |
|---|---|---|---|---|---|---|
| EtOH | SEQ ID NO: 19 | SEQ ID NO: 19 (aa 1-438) | JA308 SEQ ID NO: 7 | JA308 SEQ ID NO: 1 (aa 20-496) | JA503 SEQ ID NO: 8 | JA514 SEQ ID NO: 9 |
| w/o EtOH | 0.93 | 0.93 | 1.03 | 0.99 | 0.94 | 0.96 |
| w EtOH | 0.12 | 0.36 | 0.63 | 0.68 | 0.69 | 0.68 |

| | 20 hr | | | | | |
|---|---|---|---|---|---|---|
| EtOH | SEQ ID NO: 19 | SEQ ID NO: 19 (aa 1-438) | JA308 SEQ ID NO: 7 | JA308 SEQ ID NO: 1 (aa 20-496) | JA503 SEQ ID NO: 8 | JA514 SEQ ID NO: 9 |
| w/o EtOH | 0.63 | 0.70 | 0.90 | 0.92 | 0.83 | 0.95 |
| w EtOH | 0.00 | 0.00 | 0.05 | 0.06 | 0.07 | 0.06 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A hybrid polypeptide having alpha-amylase activity, selected from a first polypeptide sequence comprising a catalytic core, and a second polypeptide sequence comprising a carbohydrate binding module (CBM), wherein
   (a) the catalytic core is selected from a polypeptide having at least 80% sequence identity to amino acids 20 to 494 of SEQ ID NO: 1 or amino acids 20 to 496 of SEQ ID NO: 1; and
   (b) the CBM is selected from a polypeptide having at least 75% sequence identity to SEQ ID NO: 4, SEQ ID NO: 5, or SEQ ID NO: 6.

2. The hybrid alpha-amylase of claim 1, further comprising a linker comprising a sequence of from about 2 to about 100 amino acid residues.

3. The hybrid alpha-amylase of claim 2, wherein the linker is selected from a polypeptide having at least 75% sequence identity to SEQ ID NO: 2, or SEQ ID NO: 3.

4. The hybrid polypeptide of claim 1 selected from a polypeptide having 75% sequence identity to SEQ ID NO: 7, SEQ ID NO: 8, or SEQ ID NO: 9.

5. A composition comprising the polypeptide of claim 1.

6. A whole broth formulation or cell culture composition comprising the polypeptide of claim 1.

7. A process of producing a fermentation product from starch-containing material comprising the steps of: (a) liquefying starch-containing material above the initial gelatinization temperature of said starch-containing material in the presence of an alpha amylase; (b) saccharifying the liquefied material; and (c) fermenting with a fermenting organism; wherein step (b) is carried out using at least an alpha-amylase of claim 1, and optionally a glucoamylase.

8. A process of producing a fermentation product from raw starch material, comprising the steps of: (a) saccharifying starch-containing material at a temperature below the initial gelatinization temperature of said starch-containing material; and (b) fermenting with a fermenting organism, wherein step (a) is carried out using at least an alpha-amylase of claim 1, and optionally a glucoamylase.

9. A process of producing a syrup product from starch-containing material, comprising the step of: (a) liquefying starch-containing material at a temperature above the initial gelatinization temperature of said starch-containing material in the presence of an alpha amylase; (b) saccharifying the liquefied material in the presence of an alpha-amylase of claim 1, and optionally a glucoamylase.

10. A polynucleotide encoding the polypeptide of claim 1.

11. A nucleic acid construct or expression vector comprising the polynucleotide of claim 10 operably linked to one or more control sequences that direct the production of the polypeptide in an expression host.

12. A recombinant host cell comprising the polynucleotide of claim 10 operably linked to one or more control sequences that direct the production of the polypeptide.

13. The host cell according to claim 12, wherein the host cell is a yeast cell.

14. The process of claim 7, wherein a host cell comprising a polynucleotide encoding a hybrid polypeptide having alpha-amylase activity is applied in the fermentation step, wherein the polynucleotide is operably linked to one or more control sequences that direct the production of the polypeptide in the host, wherein the hybrid polypeptide having alpha-amylase activity is selected from a first polypeptide sequence comprising a catalytic core, and a second polypeptide sequence comprising a carbohydrate binding module (CBM), wherein
   (a) the catalytic core is selected from a polypeptide having at least 80% sequence identity to amino acids 20 to 494 of SEQ ID NO: 1 or amino acids 20 to 496 of SEQ ID NO: 1; and
   (b) the CBM is selected from a polypeptide having at least 75% sequence identity to SEQ ID NO: 4, SEQ ID NO: 5, or SEQ ID NO: 6.

15. A method of producing a polypeptide, comprising cultivating the host cell of claim 12 under conditions conducive for production of the polypeptide.

16. A transgenic plant, plant part or plant cell comprising the polynucleotide of claim 10.

17. The hybrid polypeptide of claim 1, wherein the catalytic core is selected from a polypeptide having at least 85% identity to SEQ ID NO: 1 or amino acids 20 to 496 of SEQ ID NO: 1, and the CBM is selected from a polypeptide having at least 80% sequence identity to SEQ ID NO: 4, SEQ ID NO: 5, or SEQ ID NO: 6.

18. The hybrid polypeptide of claim 1, wherein the catalytic core is selected from a polypeptide having at least 90% identity to SEQ ID NO: 1 or amino acids 20 to 496 of SEQ ID NO: 1, and the CBM is selected from a polypeptide having at least 85% sequence identity to SEQ ID NO: 4, SEQ ID NO: 5, or SEQ ID NO: 6.

19. The hybrid polypeptide of claim 1, wherein the catalytic core is selected from a polypeptide having at least 90% identity to SEQ ID NO: 1 or amino acids 20 to 496 of SEQ ID NO: 1, and the CBM is selected from a polypeptide having at least 90% sequence identity to SEQ ID NO: 4, SEQ ID NO: 5, or SEQ ID NO: 6.

20. The hybrid polypeptide of claim 1, wherein the catalytic core is selected from a polypeptide having at least 95% identity to SEQ ID NO: 1 or amino acids 20 to 496 of SEQ ID NO: 1, and the CBM is selected from a polypeptide having at least 95% sequence identity to SEQ ID NO: 4, SEQ ID NO: 5, or SEQ ID NO: 6.

* * * * *